(12) United States Patent
Fink et al.

(10) Patent No.: US 9,365,013 B2
(45) Date of Patent: Jun. 14, 2016

(54) MULTIMATERIAL THERMALLY DRAWN PIEZOELECTRIC FIBERS

(75) Inventors: Yoel Fink, Brookline, MA (US); Zheng Wang, Austin, TX (US); Shunji Egusa, Cleveland Heights, OH (US); Noémie Chocat, Paris (FR); John D. Joannopoulos, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1068 days.

(21) Appl. No.: 13/178,109

(22) Filed: Jul. 7, 2011

(65) Prior Publication Data

US 2014/0025007 A1    Jan. 23, 2014

Related U.S. Application Data

(60) Provisional application No. 61/363,152, filed on Jul. 9, 2010.

(51) Int. Cl.

| G02B 6/00 | (2006.01) |
|---|---|
| B32B 1/08 | (2006.01) |
| H01B 1/22 | (2006.01) |
| H01B 1/24 | (2006.01) |
| H01L 41/08 | (2006.01) |
| H01L 41/193 | (2006.01) |
| H01L 41/45 | (2013.01) |
| H04R 17/00 | (2006.01) |
| A61M 5/14 | (2006.01) |
| B29D 99/00 | (2010.01) |
| H01B 3/30 | (2006.01) |

(Continued)

(52) U.S. Cl.
CPC .. *B32B 1/08* (2013.01); *A61M 5/14* (2013.01); *B29D 99/0078* (2013.01); *H01B 1/22* (2013.01); *H01B 1/24* (2013.01); *H01B 3/30* (2013.01); *H01L 41/082* (2013.01); *H01L 41/193* (2013.01); *H01L 41/45* (2013.01); *H04R 17/00* (2013.01); *B82Y 30/00* (2013.01); *H04R 17/10* (2013.01); *H04R 2217/03* (2013.01); *Y10T 428/2935* (2015.01); *Y10T 428/2944* (2015.01); *Y10T 428/2964* (2015.01); *Y10T 428/2967* (2015.01)

(58) Field of Classification Search
CPC .......................................................... G02B 6/00
USPC ........................................................... 385/123
See application file for complete search history.

(56) References Cited

U.S. PATENT DOCUMENTS

| 3,854,112 A * | 12/1974 | Greenwood .................... 338/47 |
|---|---|---|
| 3,975,698 A | 8/1976 | Redman |
| 4,726,651 A | 2/1988 | Wei et al. |

(Continued)

OTHER PUBLICATIONS

Abouraddy, Ayman F. et al., "Large-scale optical-field measurements with geometric fibre constructs," Nature Materials 5: 532-536 (2006).

(Continued)

*Primary Examiner* — Kaveh C Kianni
(74) *Attorney, Agent, or Firm* — Theresa A. Lober

(57) ABSTRACT

Disclosed are fibers that include a composite of at least three different materials, where the at least three different materials include a conductor, an insulator, and a non-centrosymmetric material, and where each material is disposed in one or more different cross-sectional regions of the fiber, with each region extending along a common length of the fiber.

90 Claims, 17 Drawing Sheets

(51) Int. Cl.
B82Y 30/00 (2011.01)
H04R 17/10 (2006.01)

(56) References Cited

U.S. PATENT DOCUMENTS

| | | | |
|---|---|---|---|
| 4,742,318 A | 5/1988 | Jen et al. | |
| 4,823,041 A | 4/1989 | Inoue et al. | |
| 5,072,035 A | 12/1991 | Chen et al. | |
| 5,135,295 A | 8/1992 | Jen et al. | |
| 5,152,291 A | 10/1992 | Dias | |
| 5,636,299 A * | 6/1997 | Bueno et al. | 385/15 |
| 5,867,268 A | 2/1999 | Gelikonov et al. | |
| 6,337,835 B1 | 1/2002 | Sporn et al. | |
| 6,385,377 B1 | 5/2002 | Brueck et al. | |
| 6,620,287 B2 | 9/2003 | Cass | |
| 6,801,698 B2 | 10/2004 | King et al. | |
| 7,047,800 B2 | 5/2006 | Thiesen et al. | |
| 7,292,758 B2 * | 11/2007 | Bayindir et al. | 385/101 |
| 7,295,734 B2 * | 11/2007 | Bayindir et al. | 385/101 |
| 7,567,740 B2 * | 7/2009 | Bayindir et al. | 385/101 |
| 7,629,727 B2 | 12/2009 | Whinnery | |
| 2002/0182397 A1 * | 12/2002 | Whatley | 428/297.4 |
| 2003/0141785 A1 | 7/2003 | Sato et al. | |
| 2003/0169315 A1 | 9/2003 | Pickrell | |
| 2004/0123946 A1 | 7/2004 | Cass | |
| 2005/0053345 A1 * | 3/2005 | Bayindir et al. | 385/123 |
| 2007/0019917 A1 * | 1/2007 | Bayindir et al. | 385/123 |
| 2008/0087047 A1 * | 4/2008 | Bayindir et al. | 65/389 |
| 2009/0056094 A1 | 3/2009 | Shi et al. | |
| 2009/0085444 A1 | 4/2009 | Rivera et al. | |
| 2009/0097805 A1 * | 4/2009 | Bayindir et al. | 385/101 |
| 2009/0169158 A1 * | 7/2009 | Bayindir et al. | 385/101 |
| 2010/0097292 A1 | 4/2010 | Peczalski | |
| 2010/0316088 A1 * | 12/2010 | Bayindir et al. | 374/100 |
| 2010/0331941 A1 * | 12/2010 | Walsh et al. | 607/126 |

OTHER PUBLICATIONS

Abouraddy, A.F. et al., "Towards multimaterial multifunctional fibres that see, hear, sense and communicate," Nature Materials 6: 336-347 (2007).
Adler, Desmond C. et al., "Three-dimensional endomicroscopy using optical coherence tomography," Nature Photonics 1: 709-716 (2007).
Bayindir, Mehmet et al., "Metal-insulator-semiconductor optoelectronic fibers," Nature 431: 826-829 (2004).
Bayindir, Mehmet et al., "Integrated fibres for self-monitored optical transport," Nature Materials 4: 820-825 (2005).
Benoit, Gilles et al., "Static and Dynamic Properties of Optical Microcavities in Photonic Bandgap Yarns," Advanced Materials 15(24): 2053-2056 (2003).
Benoit, Gilles et al., "Dynamic all-optical tuning of transverse resonant cavity modes in photonic bandgap fibers," Optics Letters 30(13): 1620-1622 (2005).
Bergot, M.-V. et al., "Generation of permanent optically induced second-order nonlinearities in optical fibers by poling," Optics Letters 13(7): 592-594 (1988).
Bune, A.V. et al., "Two-dimensional ferroelectric films," Nature 391: 874-877 (1998).
Carpi, Federico et al., "Electroactive Polymer-Based Devices for e-Textiles in Biomedicine," IEEE Transactions on Information Technology in Biomedicine 9(3): 295-318 (2005).
Davis, G.T. et al., "Electric-field-induced phase changes in poly(vinylidene fluoride)," Journal of Applied Physics 49(10): 4998-5002 (1978).
Deng, D.S. et al., "In-Fiber Semiconductor Filament Arrays," Nano Letters 8(12): 4265-4269 (2008).
Fokine, M. et al., "Integrated fiber Mach-Zehnder interferometer for electro-optic switching," Optics Letters 27(18): 1643-1645 (2002).
Furukawa, Takeo, "Ferroelectric Properties of Vinylidene Fluoride Copolymers," Phase Transitions 18: 143-211 (1989).
Golubovic, B. et al., "Optical frequency-domain reflectometry using rapid wavelength tuning of a $Cr^{4+}$:forsterite laser," Optics Letters 22(22): 1704-1706 (1997).

Hart, Shandon D., "External Reflection from Omnidirectional Dielectric Mirror Fibers," Science 296: 510-513 (2002).
Huber, R. et al., "Amplified, frequency swept lasers for frequency domain reflectometry and OCT imaging: design and scaling principles," Optics Express 13(9): 3513-3528 (2005).
Kawai, Heiji, "The Piezoelectricity of Poly(vinylidene Fluoride)," Japanese Journal of Applied Physics 8: 975-976 (1969).
Kerbage, C. et al., "Integrated all-fiber variable attenuator based on hybrid microstructure fiber," Applied Physics Letters 79(19): 3191-3193 (2001).
Kimura, Kuniko et al., "Ferroelectric properties of poly(vinylidenefluoride-trifluoroethylene) copolymer thin films," Applied Physics Letters 43(9): 834-836 (1983).
Knight, Jonathan C., "Photonic crystal fibres," Nature 424: 847-851 (2003).
Koga, Keiko et al., "Piezoelectricity and related properties of vinylidene fluoride and trifluoroethylene copolymers," Journal of Applied Physics 59(6): 2142-2150 (1986).
Lando, J.B. et al., "Nuclear Magnetic Resonance and X-Ray Determination of the Structure of Poly(vinylidene Fluoride)," Journal of Polymer Science Part A-1 4: 941-951 (1966).
Lando, J.B. et al., "The Polymorphism of Poly(vinylidene fluoride). I. The Effect of Head-toHead Structure," Journal of Macromolecular Science: Physics B2(2): 205-218 (1968).
Larsen, Thomas Tanggaard et al., "Optical devices based on liquid crystal photonic bandgap fibres," Optics Express 11(20): 2589-2596 (2003).
Li, L. et al., "Broadband Metal/Glass Single-Mode Fibre Polarisers," Electronics Letters 22(19): 1020-1022 (1986).
Lovinger, Andrew J., "Ferroelectric Polymers," Science 220: 1115-1121 (1983).
Matsushige, K. et al., "The II-I crystal transformation of poly(vinylidene fluoride) under tensile and compressional stresses," Polymer 21: 1391-1397 (1980).
Neese, Bret et al., "Large Electrocaloric Effect in Ferroelectric Polymers Near Room Temperature," Science 321: 821-823 (2008).
Omote, Kenji et al., "Temperature dependence of elastic, dielectric, and piezoelectric properties of 'single crystalline' films of vinylidene fluoride trifluoroethylene copolymer," Journal of Applied Physics 81(6): 2760-2769 (1997).
Park, Youn Jung et al., "Irreversible extinction of ferroelectric polarization in P(VDF-TrFE) thin films upon melting and recrystallization," Applied Physics Letters 88: 242908 (2006).
Pinet, Eric, "Saving lives," Nature Photonics 2: 160-162 (2008).
Poole, S.B. et al., "Characterization of Special Fibers and Fiber Devices," Journal of Lightwave Technology 7(8): 1242-1255 (1989).
Robert, Michelle et al., "Fabrication of focused poly(vinylidene fluoride-trifluoroethylene) P(VDF-TrFE) copolymer 40-50 MHz ultrasound transducers on curved surfaces," Journal of Applied Physics 96(1): 252-256 (2004).
Russell, Philip, "Photonic Crystal Fibers," Science 299: 358-362 (2003).
Temelkuran, Burak et al., "Wavelength-scalable hollow optical fibres with large photonic bandgaps for $CO_2$ laser transmission," Nature 420: 650-653 (2002).
Townsend, Paul D. et al., "Measurement of the refractive-index modulation generated by electrostriction-induced acoustic waves in optical fibers," Optics Letters 21(5): 333-335 (1996).
Wang, Z.L. et al., "Piezoelectric Nanogenerators Based on Zinc Oxide Nanowire Arrays," Science 312: 242-246 (2006).
Wang, X. et al., "Direct-Current Nanogenerator Driven by Ultrasonic Waves," Science 316: 102-105 (2007).
Wegener, M. et al., "Patterned ferro-, pyro- and piezoelectricity in poly(vinylidene fluoride) by means of a laser-induced irreversible $β→α$ phase transformation," Journal of Applied Physics 91(5): 3193-3196 (2002).
Wu, C.Y. et al., "Direct image transmission through a multi-mode square optical fiber," Optics Communications 157: 17-22 (1998).

(56) References Cited

OTHER PUBLICATIONS

Wu, J. et al., "In-Situ Simultaneous Synchrotron Small- and Wide-Angle X-ray Scattering Measurement of Poly(vinylidene fluoride) Fibers under Deformation," Macromolecules 33: 1765-1777 (2000).
Yagi, Toshiharu et al., "Transition Behavior and Dielectric Properties in Trifluoroethylene and Vinylidene Fluoride Copolymers," Polymer Journal 12(4): 209-223 (1980).
Yamada, Takeshi et al., "Ferroelectric-to-paraelectric phase transition of vinylidene fluoride-trifluoroethylene copolymer," Journal of Applied Physics 52(2): 948-952 (1981).
Zhang, Q.M. et al., "Giant Electrostriction and Relaxor Ferroelectric Behavior in Electron-Irradiated Poly(vinylidene fluoride-trifluoroethylene) Copolymer," Science 280: 2101-2104 (1998).
International Search Report and Written Opinion for application no. PCT/US2011/43175, dated Mar. 12, 2012, by Lee W. Young.

* cited by examiner

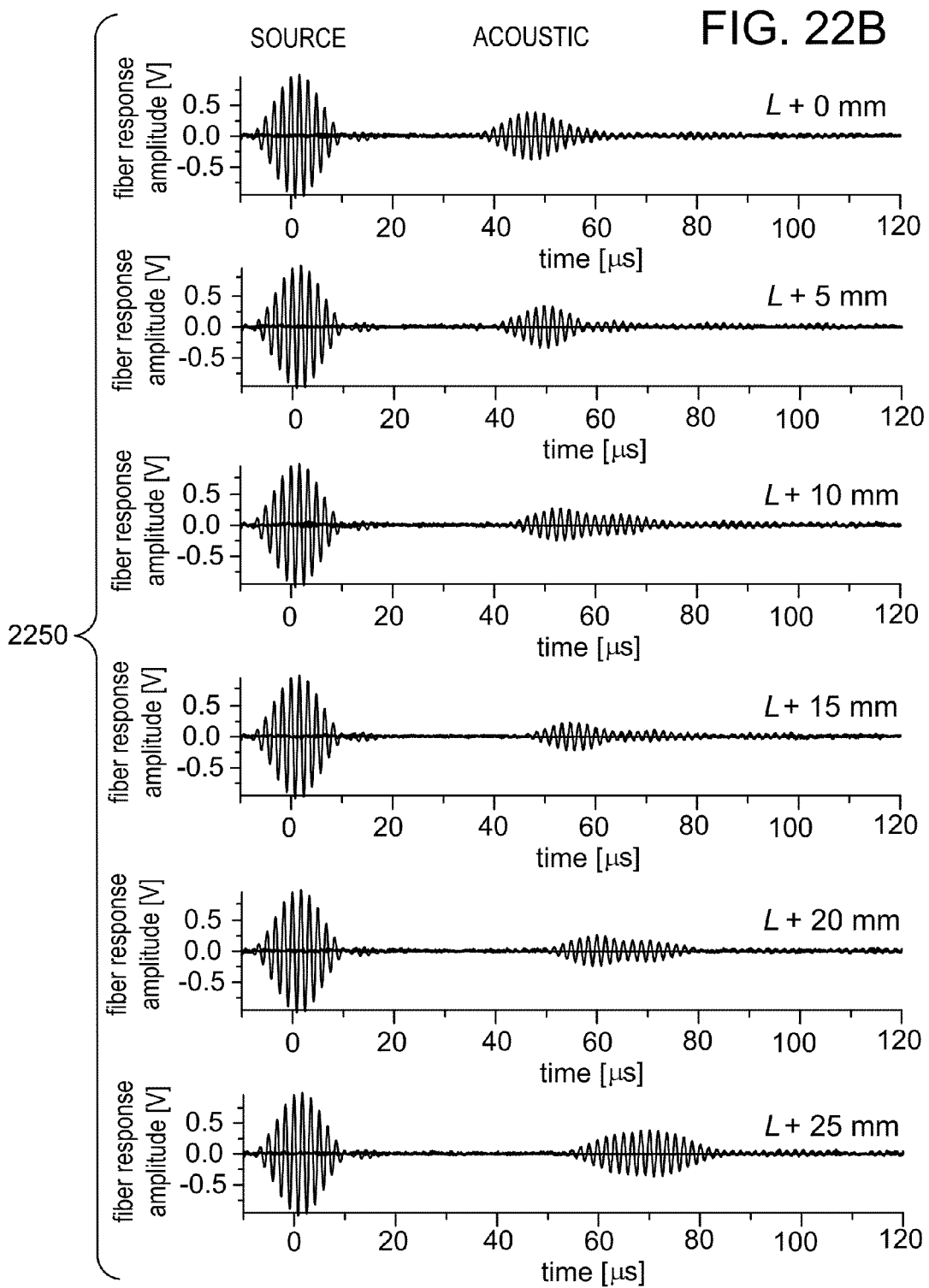

MULTIMATERIAL THERMALLY DRAWN PIEZOELECTRIC FIBERS

CROSS-REFERENCE TO RELATED APPLICATIONS

This application claims priority to U.S. Provisional Application No. 61/363,152, filed on Jul. 9, 2010, the entire contents of which are incorporated herein by reference.

STATEMENT AS TO FEDERALLY SPONSORED RESEARCH

This invention was made with government support under Grant No. DMR0213282 awarded by the National Science Foundation and under Grant No. W911NF-07-D-0004 and Contract No. DAAD19-03-1-0357 awarded by the Army Research Office. The government has certain rights in the invention.

TECHNICAL FIELD

This disclosure relates to fibers and other structures that include materials which convert electric signals to acoustic signals, and convert acoustic signals to electric signals.

BACKGROUND

Fibers are ubiquitous materials that appear in a range of applications from natural and polymeric textile fabrics used in clothes to fibers made of silica glass that carry optical signals and can be fabricated in a variety of lengths, from a few centimeters to hundreds of kilometers. Typically, fibers are made of a single material, e.g., silica glass. Recently, new classes of fibers have emerged which combine a multiplicity of different materials. The different materials are arranged in specific geometries to enable functions such as transmission or reflection of light, detection of light, and thermal detection.

SUMMARY

In a first aspect, the disclosure features fibers that include a composite of at least three different materials, where the at least three different materials include a conductor, an insulator, and a non-centrosymmetric material, and where each material is disposed in one or more different cross-sectional regions of the fiber, with each region extending along a common length of the fiber.

Embodiments of the fibers can include any one or more of the following features.

At a common fiber draw temperature, each of the at least three different materials can have a viscosity that is less than about $10^7$ Poise. At the common fiber draw temperature, each of the at least three different materials can maintain structural integrity. At the common fiber draw temperature, each of the at least three different materials can maintain its chemical composition.

The non-centrosymmetric material can include a crystalline material. The non-centrosymmetric material can include a piezoelectric material. The piezoelectric material can include a ferroelectric material.

The conductor can be a first conductor, and the fiber can include a second conductor, the second conductor being disposed in one or more additional cross-sectional regions of the fiber that extend along the common length of the fiber. The first conductor can have a viscosity that is greater than about $10^2$ Poise at the common fiber draw temperature to enable large surface area contact with the non-centrosymmetric material. The second conductor can electrically contact the first conductor along the common length of the fiber. The second conductor can have a conductivity greater than that of the first conductor to improve conductivity along the extended length of the fiber.

A first set of the cross-sectional regions can include the first and second conductors in electrical contact with one another define a first electrode, a second set of the cross-sectional regions can include the first and second conductors in electrical contact with one another define a second electrode, one of the cross-sectional regions can include the non-centrosymmetric material to define an active region, and the first and second electrodes can be positioned on opposite sides of the active region. The first conductor in each of the electrodes can contact the non-centrosymmetric material in the active region.

The fiber can include a spacer material positioned between the non-centrosymmetric material in the active region and the first conductor in each of the electrodes. The spacer material can be a thermoplastic material.

A cross-sectional shape of the conductor can have a maximum length measured along an outer surface of the conductor and a thickness measured in a direction orthogonal to the outer surface, where a ratio of the maximum length to the thickness is 3 or more. The fiber can have a length of 10 centimeters or more, and a maximum cross-sectional dimension of 2 mm or less.

The fiber can have an outer perimeter that is one of circular, elliptical, rectangular, square, triangular, and polygonal in shape. The first conductor in each of the electrodes can extend to an outer surface of the fiber along at least a portion of the common length of the fiber.

The fiber can be drawn from a preform having a length that is smaller than a length of the fiber. The at least three different materials can be disposed in an all-solid fiber cross section. The non-centrosymmetric material can sustain a field of 3 MV/m or more when an electrical potential difference is applied between the first and second electrodes.

The non-centrosymmetric material in the active region can cause an acoustic waveform to be emitted from the fiber when an electrical potential difference is applied between the first and second electrodes. A frequency of the acoustic waveform can correspond to a frequency of the electrical potential difference.

The non-centrosymmetric material in the active region can generate an electrical potential difference corresponding to an electrical waveform between the first and second electrodes when an acoustic waveform impinges on the non-centrosymmetric material. A frequency of the electrical waveform can correspond to a frequency of the acoustic waveform.

The fiber can include one or more additional regions positioned within the cross-section of the fiber and including materials with different optical properties, the one or more additional regions forming an optical transmission element extending along at least a portion of the common length of the fiber. At the common fiber draw temperature, each of the materials within the one or more additional regions can have a viscosity that is less than about $10^7$ Poise and can maintain structural integrity and chemical composition.

The fiber can include one or more additional regions positioned within the cross-section of the fiber and including materials with different optical properties, the one or more additional regions forming an optical device extending along at least a portion of the common length of the fiber. At the common fiber draw temperature, each of the materials within the one or more additional regions can have a viscosity that is less than about $10^7$ Poise and can maintain structural integrity and chemical composition.

The fiber can include one or more additional regions positioned within the cross-section of the fiber and including materials with different electrical properties, the one or more additional regions forming an electronic device extending along at least a portion of the common length of the fiber. At the common fiber draw temperature, each of the materials within the one or more additional regions can have a viscosity that is less than about $10^7$ Poise and can maintain structural integrity and chemical composition.

The insulator can include a polymeric insulating material. The polymeric insulating material can include a material having a high glass transition temperature. The polymeric insulating material can include at least one of a polyimide material, a polysulfone material, a polycarbonate material, a polymethacrylate material, a polyester material, a polyacrylate material, a polyether sulfone material, a cyclic olefin material, and a fluorinated polymer material. The polymeric insulating material can include a thermoplastic material. The insulator can include a high temperature insulating material. The high temperature insulating material can include silica and/or silica glass.

The first conductor can include a composite of a host material and conducting particulates. The host material can include at least one material selected from the group consisting of a polycarbonate material, a polyethylene material, an acrylonitrile-butadiene-styrene copolymer material, an acetal copolymer material, a polypropylene material, a polyvinylidene fluoride material, and a polyetherimide material. The conducting particulates can include at least one material selected from the group consisting of carbon particles, carbon fibers, carbon nanotubes, and stainless steel fibers. The first conductor can be more viscous than the second conductor to enable large surface area contact with the non-centrosymmetric material.

The second conductor can include one or more metals. The second conductor can include an alloy of two or more metals. The one or more metals can include at least one of bismuth, lead, tin, indium, cadmium, gallium, copper, aluminum, silver, gold, and zinc. The second conductor can be more conductive than the first conductor to decrease resistivity along the length of the fiber relative to a fiber having only the first conductor.

The non-centrosymmetric material can include at least one of a poly(vinylidene fluoride) material, a copolymer material of vinylidene fluoride and trifluoroethylene, a polyvinyl chloride material, a copolymer material of vinyl acetate and vinylidene cyanide, a nylon polymer material, a nylon copolymer material, and a polyacrylonitrile material. The non-centrosymmetric material can include a high temperature ceramic material such as lead zirconate titanate, quartz, barium titanate, and cadmium sulfide.

An electrical resistivity of the first and/or second conductor can be $10^5$ ohm·m or less. An electrical resistivity of the insulator can be $10^8$ ohm·m or more. A dielectric strength of the insulator can be 10 MV/m or more.

The fiber can include a reservoir positioned within the fiber. The reservoir can be positioned at least partially within a region that includes the insulator or at least partially within a region that includes the first conductor. The non-centrosymmetric material can form at least one wall of the reservoir.

The non-centrosymmetric material can cause an acoustic waveform to be emitted from the fiber when an electrical potential difference is applied between the first and second electrodes. The acoustic waveform can be configured to cause a substance present within the reservoir to leave the reservoir through a valve positioned in a wall of the reservoir. The valve can be positioned so that the substance leaving the reservoir emerges from an end of the fiber. The valve can be positioned so that the substance leaving the reservoir emerges into a hollow region of the fiber. The valve can include a material having a permeability for the substance that can be varied by introducing an acoustic waveform into the material. The substance can include at least one of: (a) a plurality of particles having a particle size that can be varied by introducing an acoustic waveform into the substance; (b) a viscosity that can be varied by introducing an acoustic waveform into the substance; and (c) a diffusivity that can be varied by introducing an acoustic waveform into the substance.

A drug delivery system can include any of the fibers disclosed herein, and an electrical source coupled to the fiber(s) to selectively cause delivery of a drug material in the reservoir.

An acoustic wave detector can include any of the fibers disclosed herein, and an electrical detector coupled to the fiber(s) to detect an electrical signal produced by the non-centrosymmetric material in response to the acoustic wave. The detector can include a plurality of fibers, wherein the plurality of fibers can be configured to form a fiber array.

An acoustic wave generator can include any of the fibers disclosed herein, and an electrical source coupled to the fiber(s) to selectively cause the non-centrosymmetric material in the fiber(s) to generate the acoustic wave.

Embodiments of the fibers can also include any of the other features or aspects disclosed herein, as appropriate.

In another aspect, the disclosure features methods for producing fibers that include a composite of at least three different materials, the methods including: (a) assembling a fiber preform that includes the at least three different materials, where the at least three different materials include a conductor, an insulator, and a non-centrosymmetric material; and (b) drawing the preform at a fiber draw temperature into a fiber that includes each of the at least three different materials disposed in one or more different cross-sectional regions of the fiber.

Embodiments of the methods can include any one or more of the following features.

At the fiber draw temperature, each of the at least three different materials can have a viscosity that is less than about $10^7$ Poise. Each of the at least three different materials can maintain structural integrity and chemical composition when the preform is drawn into the fiber.

The method can include maintaining a drawing tension of 5 grams or more per square millimeter of the preform cross-sectional area as the preform is drawn to form the fiber. The method can include cooling the fiber after the preform is drawn, where the non-centrosymmetric material solidifies in a non-centrosymmetric solid phase when the fiber is cooled. The method can include annealing the fiber for a period of one hour or more at a temperature of between 120° and 150° C.

A cross-sectional region that includes the non-centrosymmetric material can define an active region, and the conductor can be disposed in a first set of cross-sectional regions that define a first electrode, and in a second set of cross-sectional regions that define a second electrode, the first and second electrodes being positioned on opposite sides of the active region.

The method can include applying an electrical potential difference between the first and second electrodes to align domains within the non-centrosymmetric material. Applying the electrical potential difference can include applying a direct current potential difference of 10 V or more per micrometer of thickness of the non-centrosymmetric material.

The relative positions and cross-sectional dimensions of each of the at least three different materials can be substantially the same in the preform and the fiber. The fiber can have a length that is at least about 100 times greater than a length of the preform. The fiber can have a maximum cross-sectional dimension that is at least about 10 times smaller than a maximum cross-sectional dimension of the preform.

The method can include consolidating the preform prior to drawing the preform into a fiber. Consolidating the preform can include heating the preform under vacuum.

The fiber draw temperature can be greater than a melting temperature or a glass transition temperature of the conductor. The fiber draw temperature can be between about 120° C. and about 500° C.

The preform can have a length of less than 50 cm. The preform can be drawn to form a fiber having a length of 1 meter or more.

The insulator can include a polymeric insulating material. The polymeric insulating material can include at least one of a polyimide material, a polysulfone material, a polycarbonate material, a polymethacrylate material, a polyester material, a polyacrylate material, a polyether sulfone material, a cyclic olefin material, and a fluorinated polymer material. The insulator can include a high temperature insulating material. The high temperature insulating material can include silica and/or silica glass.

The conductor can include a composite of a host material and conducting particulates. The host material can include at least one material selected from the group consisting of a polycarbonate material, a polyethylene material, an acrylonitrile-butadiene-styrene copolymer material, an acetal copolymer material, a polypropylene material, a polyvinylidene fluoride material, and a polyetherimide material. The conducting particulates can include at least one material selected from the group consisting of carbon particles, carbon fibers, carbon nanotubes, and stainless steel fibers.

The conductor can be a first conductor, and the at least three different materials can include a second conductor disposed in one or more additional cross-sectional regions of the fiber. The second conductor can be disposed in the first and second sets of cross-sectional regions. The second conductor can include one or more metals. The one or more metals can include at least one of bismuth, lead, tin, indium, cadmium, gallium, copper, aluminum, silver, gold, and zinc. The first conductor can have a viscosity that is greater than about $10^2$ Poise at the fiber draw temperature. Specifically, the first conductor can be more viscous than the second conductor to enable large surface area contact with the non-centrosymmetric material, while the second conductor can be more conductive than the first conductor to decrease resistivity along the length of the fiber relative to a fiber having only the first conductor.

The second conductor can electrically contact the first conductor in the first and second sets of cross-sectional regions. The first conductor in each of the first and second sets of cross-sectional regions can contact the non-centrosymmetric material in the active region.

The at least three materials can include a spacer material positioned between the non-centrosymmetric material in the active region and the first conductor in each of the electrodes. The spacer material can include a thermoplastic material.

The non-centrosymmetric material can include a crystalline material. The non-centrosymmetric material can include at least one of a poly(vinylidene fluoride) material, a copolymer material of vinylidene fluoride and trifluoroethylene, a polyvinyl chloride material, a copolymer material of vinyl acetate and vinylidene cyanide, a nylon polymer material, a nylon copolymer material, and a polyacrylonitrile material. The non-centrosymmetric material can include a high temperature ceramic material such as lead zirconate titanate, quartz, barium titanate, and cadmium sulfide.

The method can include applying an oxidation inhibitor to the second conductor prior to drawing the preform into a fiber. The method can include applying a wetting promoter to the second conductor prior to drawing the preform into a fiber. The method can include applying a flux to the second conductor prior to drawing the preform into a fiber.

Assembling the fiber preform can include wrapping a layer of one of the materials around another one of the materials. Assembling the fiber preform can include evaporating a layer of one of the materials or a semiconducting material onto another one of the materials. Assembling the fiber preform can include at least one of: (a) evaporating one or more layers of the conductor onto the non-centrosymmetric material; and (b) wrapping one or more layers of the conductor around the non-centrosymmetric material. Assembling the fiber preform can include at least one of: (a) evaporating a layer of the insulator onto the conductor; and (b) wrapping a layer of the insulator around the conductor.

The conductor can be a first conductor and the at least three materials can include a second conductor, and assembling the fiber preform can include applying the second conductor to a portion of a surface of the first conductor. Applying the second conductor to a portion of the surface of the first conductor can include applying a liquid polymer solution to the portion of the surface of the first conductor, and positioning the second conductor to contact at least a portion of the liquid polymer solution on the first conductor. The first and second conductors can extend substantially along the entire length of the drawn fiber.

Assembling the fiber preform can include positioning a sacrificial preform element within the preform to define a hollow fiber region, and removing the sacrificial preform element prior to drawing the preform.

Unless otherwise defined, all technical and scientific terms used herein have the same meaning as commonly understood by one of ordinary skill in the art to which this disclosure belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and description. Other features and advantages will be apparent from the description, drawings, and claims.

DESCRIPTION OF DRAWINGS

FIG. 22B is a series of plots showing response amplitude as a function of time delay for a piezoelectric fiber.

Like reference symbols in the various drawings indicate like elements.

DETAILED DESCRIPTION

Figure 1A:
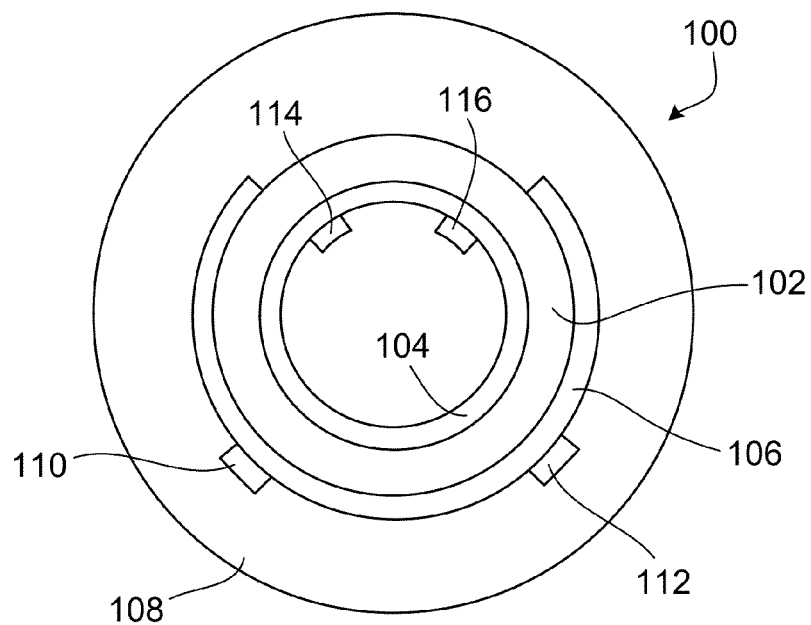
FIG. 1A is a cross-sectional view of a fiber.

Fibers have been produced in a wide range of geometries and configurations, and can include many different materials. For example, U.S. Pat. No. 7,295,734 discloses fibers that include conducting, insulating, and semiconducting materials. The fibers are fabricated from preforms and drawn out to extended lengths so that the diameter of the drawn fiber can be smaller than the diameter of the preform by a factor of 10 or more. Methods for fabricating such fibers are disclosed, for example, in U.S. Pat. No. 7,295,734, and in U.S. Patent Application Publication No. US 2008/0087047, the entire contents of each of which are incorporated herein by reference.

However, typical fibers are not configured to either electrically generate or electrically detect acoustic waveforms, in part because such fibers are not able to convert acoustic waveforms to electrical signals and vice versa. The materials which are present in conventional fibers can include materials with varying degrees of electrical conductivity, indices of refraction, and other physical, optical, and electronic properties. In general, such materials are not capable of interconverting between acoustic and electrical waveforms.

A potential route to fabricating fibers with acoustic transduction capability (e.g., fibers that can convert acoustic signals to electrical signals, and vice versa) would be to introduce piezoelectric materials into the fibers. Embedded piezoelectric domains or regions would allow fibers to be electrically actuated over a broad range of frequencies, and would also allow fibers to function as sensitive acoustic detectors. Unfortunately, for the most part fibers have thus far been made of materials in disordered, glassy states, precluding the crystalline symmetry that is required for piezoelectricity.

Just as there are many benefits arising from the ability to propagate optical signals along extended lengths of optical fiber, it would also be beneficial to be able to generate and/or detect acoustic waveforms in fibers by electrically contacting such fibers. The present disclosure features multimaterial piezoelectric fibers and fabrication methods for constructing fibers with engineered acoustic properties. The fibers permit generation of acoustic signals along their lengths and thereby function as extended electrical-acoustic transducers. The fibers also permit detection of acoustic signals present in the fibers by converting the acoustic signals to electrical signals. The embedded piezoelectric element(s) can be integrated with other multimaterial fiber elements, including other acoustic elements and/or optical elements such as Fabry-Perot cavities and photonic bandgap structures. These combinations of fibers and other elements can be used for a variety of applications, including tunable dispersion optical transmission devices, fabrics that can rapidly modulate incoming optical signals, and forming fabric arrays for large-area detection and/or transmission of acoustic waves.

In some embodiments, the fibers disclosed herein include one or more piezoelectric materials. The piezoelectric effect is well known in certain materials and provides for the conversion of electrical energy to acoustic energy; piezoelectric devices which perform this conversion are often referred to as transducers. In a typical transducer, a piezoelectric material is positioned between two electrodes. When a mechanical stress or strain is applied to the piezoelectric material, the material generates an electrical signal in the form of surface charge that can be measured across the two electrodes. This is referred to as the direct piezoelectric effect. Such transducers are also capable of operating according to the reverse piezoelectric effect; that is, applying a variable electric field across the electrodes produces an acoustic signal in the form of a mechanical stress or strain waveform in the piezoelectric material.

Conventional piezoelectric transducers can be constructed from a variety of known piezoelectric materials, including lead zirconate titanate (PZT) and poly(vinylidene fluoride). These materials can generate and propagate acoustic signals over a broad range of frequencies from the mHz region to several GHz. However, in most piezoelectric transducers, relatively large driving voltages are used to generate acoustic signals in the piezoelectric material. Further, the brittleness of certain ceramic piezoelectric materials and challenges associated with processing such materials have limited device geometries, length scales, and, as a result, applications.

In general, the multimaterial piezoelectric fibers disclosed herein are flexible and can be extended to long lengths by heating and drawing from a fiber preform. Moreover, driving voltages can be kept relatively low by using high aspect ratio electrodes with large surface areas. In this manner, acoustic signals can be readily introduced into the fibers, and can be efficiently transmitted over long fiber lengths. The enhanced acoustic transmission properties of the fibers disclosed herein enable a variety of new applications.

Thermal drawing of a piezoelectric fiber raises a number of challenges, which span a wide range of length scales. On the hundreds of microns size-level, the necessity to utilize crystalline materials both for the piezoelectric layer and the electrical conductors can lead to the formation of multiple adjacent low viscosity domains of high aspect ratio. These domain can undergo a significant reduction in cross sectional dimensions (during the fiber draw) and are susceptible to capillary breakup and mixing due to flow instabilities. Also, at the tens of microns size-level, layer thickness variations either in the lateral or in the longitudinal directions can preclude the formation of the coercive field needed for poling. Finally on the length scale of the molecular spacing, even if capillary breakup were kinetically averted and uniform sections of fibers at metre lengths were to emerge they might not exhibit piezoelectricity because the stress and strain conditions necessary to induce the thermodynamic phase transition in PVDF cannot be sustained in the fiber draw process leading to a non-polar phase.

To address these challenges, certain embodiments disclosed here include a viscous and conductive polymer, such as a carbon-loaded poly(carbonate) (CPC), that is used to confine a low viscosity crystalline piezoelectric layer during the draw process. For example, the CPC layers exhibit high viscosity ($10^5$~$10^6$ Pa·s) at the draw temperature and adequate resistivity (1~$10^4$ ohm·m) over the frequency range from DC to tens of MHz, thus facilitating short range (hundreds of microns) charge transport on length scales associated with the fiber cross section. Furthermore, more conductive metallic filaments (such as indium filaments) can be assembled within a surrounding poly(carbonate) (PC) cladding to function as a second conductor contacting the CPC viscous conductor to thereby improve conductivity over the entire length of the fiber. Finally, a piezoelectric polymer which crystallizes into the appropriate phase is used. Specifically, poly(vinylidene fluoride-trifluoroethylene) copolymer (P(VDF-TrFE)) assumes the ferroelectric β phase spontaneously upon solidification from the melt without necessitating any mechanical stress, making it particularly suitable for the thermal fiber drawing process.

As used herein, a fiber is a structure that extends along a first direction (the fiber axis), and has a maximum cross-sectional dimension extending along a second direction orthogonal to the first direction, where a length of the fiber along the first direction is larger than the fiber's maximum cross-sectional dimension by a factor of 1000 or more.

A non-centrosymmetric material is a material having a microscopic structure that lacks inversion symmetry, as determined by x-ray diffraction, and therefore can have a macroscopic polarization. Non-centrosymmetric materials in the fibers disclosed herein can either be non-centrosymmetric at the time the fiber is drawn from a preform, or they can be centrosymmetric when drawn and later rendered non-centrosymmetric (e.g., by crystallization from a molten amorphous phase into a non-centrosymmetric crystalline solid phase).

A piezoelectric material is a material that generates an electrical signal in response to an applied mechanical stress or strain. Piezoelectric materials also exhibit the reverse piezoelectric effect: application of a varying electric field across the material generates an acoustic signal in the form of a mechanical stress or strain in the material.

A conductive material is a material that has a bulk resistivity of $10^5$ ohm·m or less at 20° C. An insulating material is a material that has a bulk resistivity of $10^8$ ohm·m or more at 20° C.

Figure 1B:
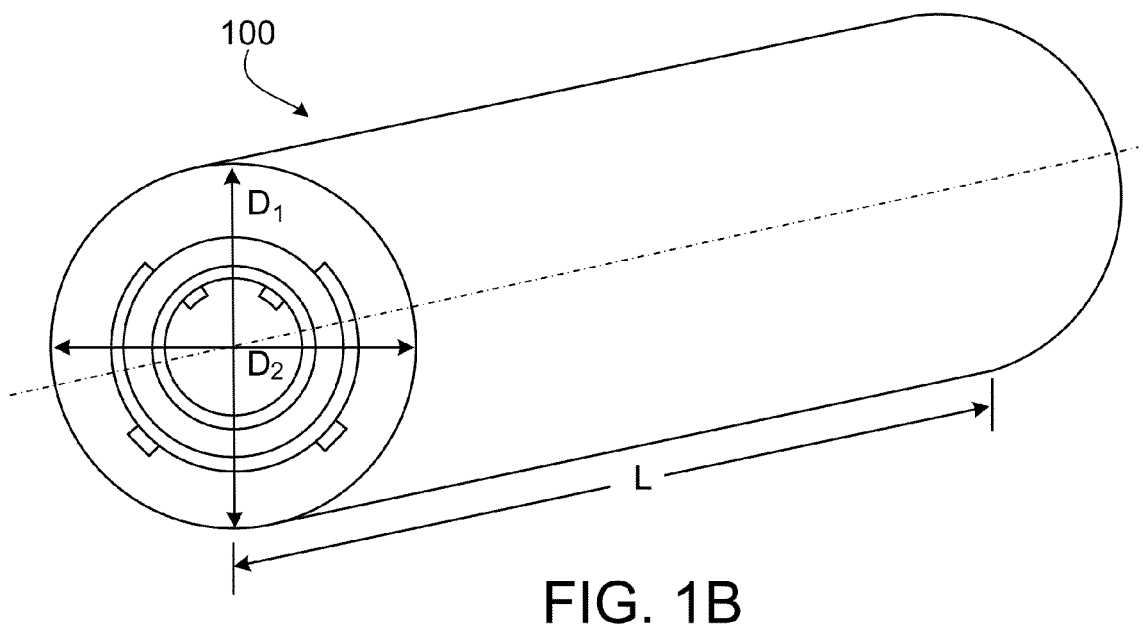
FIG. 1B is a perspective view of the fiber shown in FIG. 1A.

FIG. 1A shows a cross-sectional view of an acoustic fiber 100, and FIG. 1B shows a perspective view of the same fiber. In general, as shown in FIG. 1A, fiber 100 features a composite structure formed of a variety of materials, each material being disposed in one or more different cross-sectional regions of the fiber. In FIG. 1A, fiber 100 includes a region 102 that includes a non-centrosymmetric material, regions 104 and 106 that include a first conductor, and a region 108 that includes an insulator. Fiber 100 also includes regions 110, 112, 114, and 116 that include a second conductor. In fiber 100, region 102 with the non-centrosymmetric material forms an active region. The first conductor in regions 104 and 106 directly contacts the non-centrosymmetric material in region 102. The non-centrosymmetric material, the first conductor, and the insulator are disposed within the cross-section of fiber 100 to yield an all-solid fiber cross section.

Fiber 100 extends for a length L along a fiber axis. In cross-section, fiber 100 has a maximum dimension $D_1$ measured along a first cross-sectional dimension, and a minimum dimension $D_2$ measured along a second cross-sectional dimension. The first and second cross-sectional dimensions are both orthogonal to the fiber axis. As shown in FIGS. 1A and 1B, regions 102, 104, 106, 108, 110, 112, 114, and 116 (including the first and second conductors, the insulator, and the non-centrosymmetric material) extend along a common length of fiber 100; this common length, in turn, extends substantially along the entire length of fiber 100.

Fiber 100 is configured so that by applying a time-varying electric field between regions 104 and 106, an acoustic waveform can be generated in the active region 102 in the non-centrosymmetric material via the reverse piezoelectric effect (e.g., when the non-centrosymmetric material is a piezoelectric material). Further, when the non-centrosymmetric material is a piezoelectric material and an acoustic perturbation is introduced into the material (e.g., when a mechanical stress or strain is introduced into the fiber), the non-centrosymmetric material can generate an electric field between regions 104 and 106 that can be detected by measuring the potential difference between these regions. In fiber 100, a first set of regions 104, 114, and 116 forms a first electrode in contact with the non-centrosymmetric material in active region 102. A second set of regions 106, 110, and 112 forms a second electrode in contact with the non-centrosymmetric material in active region 102. The electrical potential difference generated by an acoustic waveform in the active region can be measured between the first and second electrodes by electrically contacting the electrodes.

To efficiently generate acoustic waveforms in piezoelectric non-centrosymmetric materials, it is important that a time-varying electric field is applied over a relatively large area of the piezoelectric material. Accordingly, in fiber 100, large-aspect ratio conductors in regions 104 and 106 that extend substantially along the entire length of fiber 100 are used to apply the electric field across the non-centrosymmetric material in active region 102. Further, to ensure efficient electrical contact between the first conductor in regions 104 and 106, and the second conductor in regions 110, 112, 114, and 116, the second conductor in each of regions 110, 112, 114, and 116 directly contacts the first conductor in either region 104 or 106 and extends substantially along the entire length of fiber 100.

The fibers disclosed herein are produced according to a thermal drawing process from pre-assembled fiber preforms. Preforms are typically constructed by assembling multiple solid materials with different electrical, optical, and mechanical properties into a single macroscopic structure. The macroscopic structure is then scaled down via a drawing process at elevated temperature to a diameter that is reduced by a factor of 10 or more. During this scaling down, the relative geometrical cross-sectional arrangement of materials in the fiber preform is preserved. Thus, devices with different electrical, optical, and acoustic properties can be constructed as preforms, and then implemented in fiber form over length scales of tens of meters or more. Moreover, these fiber-based devices can be produced at low cost, and can exhibit structural flexibility and good uniformity along their lengths.

The process of drawing long lengths of fibers from macroscopic preforms yields large area functional surfaces. Thus, for example, by drawing a preform that includes a first conductor in regions 104 and 106 into a fiber, the first conductor can contact the non-centrosymmetric material in active region 102 over a significant fraction of the non-centrosymmetric material's entire surface area. As a result, the first conductor in regions 104 and 106 can be used to efficiently generate acoustic waveforms in the non-centrosymmetric material, and can be used to detect acoustic waveforms in the non-centrosymmetric material with relatively high sensitivity. In piezoelectric fiber devices, as discussed above, conductors that directly contact the piezoelectric material over a large surface area can generate large-amplitude mechanical responses in the piezoelectric material at relatively low driving voltages. By introducing such large area conductors, acoustic waveforms can be generated in the fibers disclosed herein at relatively moderate voltages. In contrast, conventional piezoelectric transducers are typically low surface area devices due to the difficulty of fabricating large-area sandwich arrays of piezoelectric materials and electrodes. Furthermore, as the size of such conventional transducers increases, the required driving voltage increases dramatically to the order of several hundreds of volts for the largest transducers.

In some embodiments, the material that forms the first conductor in regions 104 and 106 is selected so that it remains sufficiently viscous at the thermal drawing temperature so that the first conductor does not undergo significant capillary break-up at the thermal drawing temperature. By avoiding such break-up, the first conductor maintains a large surface area contact with the non-centrosymmetric material in region 102. In some cases, however, the high viscosity materials selected to form the first conductor may not be as electrically conductive as other lower viscosity materials. Accordingly, regions 110, 112, 114, and 116 may each be smaller in cross-sectional area than regions 104 and 106, and the material that forms the second conductor in these regions can be selected on the basis of a higher conductivity than the material in regions 104 and 106 (e.g., the first conductor). The second conductor in regions 110, 112, 114, and 116 contacts the first conductor in regions 104 and 106 along the length of fiber 100.

By including a high conductivity material in regions 110, 112, 114, and 116, the overall electrical conductivity of the entire fiber can be improved along its entire (e.g., relative to fibers with only the first conductor in regions 104 and 106). Through suitable selection of materials, the first and second conductors together form electrodes that provide both a high surface area of contact with the non-centrosymmetric material, and high electrical conductivity extending along the length of the fiber.

Figure 2:
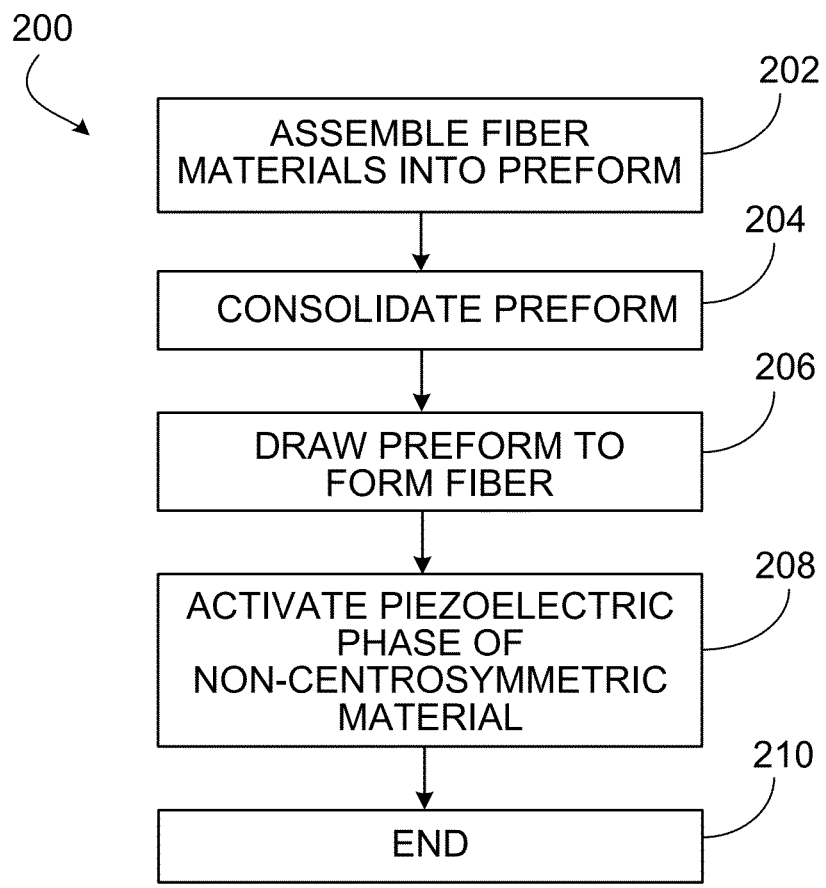
FIG. 2 is a flow chart showing a series of steps in a fiber fabrication process.

FIG. 2 includes a flow chart 200 showing a series of steps that can be used to fabricate the fibers disclosed herein. In the first step 202, the materials used to form a fiber are assembled into a preform. The preform is typically similar in both relative geometry and composition to the final fiber, but is much larger in cross-sectional dimensions and shorter in length. Typically, for example, the preform has a length from about 2 to about 100 times its maximum cross-sectional dimension. To form the fibers disclosed herein, the assembled preform includes a non-centrosymmetric material, a conductor, an insulator, and optionally a second conductor. These materials are assembled in a macroscopic structure with a cross-sectional appearance similar to that shown in FIG. 1A.

Assembly of the various materials into the preform typically involves wrapping layers of one or more of the preform materials around other preform materials, and/or evaporating layers of one or more of the preform materials onto other preform materials. Referring to FIG. 1A, for example, assembly of a preform corresponding to fiber 100 can include wrapping layers of the first conductor onto the non-centrosymmetric material in active region 102 to form regions 104 and 106. Alternatively, or in addition, assembly of the preform can include evaporating layers of the first conductor onto the interior and exterior surfaces of the non-centrosymmetric material to form regions 104 and 106. Similarly, assembling the preform can include wrapping a layer of the insulator around region 106 to form region 108, and/or evaporating a layer of the insulator onto region 106 to form region 108.

One or more semiconductors can also be wrapped and/or evaporated onto materials during preform fabrication. Exemplary semiconductors that can be introduced into performs include glassy semiconductors such as chalcogenide glasses.

To wrap layers of the various preform materials, the material to be wrapped is typically formed into a sheet (e.g., a polymer film) and then rolled around the surface of the preform to add a layer to the preform. Sheets can also be rolled around individual preform materials before they are assembled into the preform to yield multiple functional regions within a single preform.

A variety of different vapor deposition techniques can also be used to deposit preform materials. Thermal evaporation, chemical vapor deposition, sputtering, and other similar techniques can be used for form layers of materials in performs. Thermal deposition, for example, can be carried out with conventional hot filament evaporation techniques at reduced pressure (e.g., at a pressure of $10^{-4}$ Torr or less). Vacuum evaporators (e.g., Ladd Industries Model 30000) can be used in this process.

Certain conductors can oxidize when exposed to high annealing and/or drawing temperatures. Oxidized materials may not melt or flow uniformly, resulting in nonuniformities within drawn fibers. Thus, in some embodiments, one or more of various methods can be used to avoid oxidized materials in fiber preforms. In certain embodiments, for example, an oxidation inhibitor can be used to prevent oxidation of preform materials. The oxidation inhibitor, which can also be a surface wetting promoter, can be incorporated into the preform at interfaces between some or all of the conductors and other preform materials. The oxidation inhibitor can be physically applied to the conductors during preform assembly.

In some embodiments, the oxidation inhibitor is a flux (e.g., a synthetic carboxylic acid-containing fluid or a natural rosin flux). Fluxes enhance wetting of preform materials by the conductors and help to prevent capillary breakup of the conductors during drawing. Exemplary fluxes that can be used include Superior No. 312 and/or Superior No. 340 (both available from Superior Flux and Manufacturing Company, Cleveland, Ohio). Fluxes can be applied directly to the surfaces of conductors and/or to surfaces of other preform materials that will contact the conductors in the assembled preform.

In certain embodiments, oxidation inhibitors can be added directly to the conductors or to other materials in the preform. For example, an oxidation inhibitor can be added to a material that will directly contact one or more conductors in the assembled preform. The oxidation inhibitor can naturally locate at the surface of the material to which it is added, facilitating its action on the conductor in the preform. Alternatively, or in addition, a polymer, a semiconductor, or another material that inhibits oxidation can be included within the preform as a layer in contact with one or more conductors. Materials such as polymers can be applied to various preform materials by wrapping and/or vapor deposition, as discussed above, and/or by other processes such as dip coating.

In some embodiments, a fiber preform can be assembled around a sacrificial preform element. Such sacrificial element can be included in the preform to define spaces in the drawn fiber. For example, a mandrel, rod, or tube can be included in a preform to define a central hollow region of the drawn fiber. When a sacrificial element is included in a preform, consolidation of the preform (to be discussed later) typically occurs at a temperature below the glass transition temperature of the sacrificial element so that the element maintains its structural integrity.

In general, materials with poor surface adhesion that can withstand consolidation can be used as sacrificial elements. Examples of sacrificial elements that can be used in the performs disclosed herein include Teflon™ rods, tubes, and other structures. Teflon™ elements are typically removed shortly after consolidation (and prior to drawing) while the preform is still hot and slightly expanded, facilitating removal of the sacrificial element.

In some embodiments, sacrificial elements can be removed from fiber performs prior to drawing using other techniques. For example, sacrificial elements formed from materials such as quartz, glass, and other amorphous substances can be removed from fiber performs via chemical etching. Etching solutions that selectively target the material of the sacrificial element (e.g., hydrofluoric acid and/or other acid baths) can be used to remove such elements. Dry etching techniques can also be used to remove sacrificial elements provided they can selectively attack the elements in the preform.

Next, in optional step 204, the preform can be consolidated. Consolidation can include, for example, heating and/or pressurizing the preform so that that the assembled materials in the preform fill in interstitial spaces within the preform and contact one another over larger surface areas. Typically, for example, fiber preforms are consolidated at temperatures of 100° C. or more (e.g., 125° C. or more, 150° C. or more, 175° C. or more, 200° C. or more, 250° C. or more, 300° C. or more, 350° C. or more). In some embodiments, consolidation occurs by heating the preform under vacuum. For example, fiber performs can be consolidated at ambient pressures of 1 Torr or less (e.g., 0.1 Torr or less, 0.01 Torr or less, $10^{-3}$ Torr or less, $10^{-4}$ Torr or less, $10^{-5}$ Torr or less, $10^{-7}$ Torr or less).

Then, in step 206, the preform is heated and/or pressurized and drawn out to an extended length to form a fiber in which the relative positions and cross-sectional dimensions of each of the materials within the preform are substantially preserved in the drawn fiber. However, because the preform is drawn to many times its initial length, the sizes of the material features in the fiber (and the fiber diameter) are many times smaller than those in the corresponding preform.

Drawing of the fiber preform is typically performed at a fiber drawing temperature of 120° C. or more (e.g., 140° C. or more, 160° C. or more, 200° C. or more, 300° C. or more) and/or 500° C. or less (e.g., 480° C. or less, 460° C. or less, 440° C. or less, 420° C. or less, 400° C. or less, 350° C. or less). In general, the drawing temperature is selected so that it exceeds the melting or glass transition temperature of the first conductor so that the first conductor flows when drawn.

A tension is generally applied along the length of the fiber preform during drawing to extend the preform's length. To draw the performs disclosed herein, draw tensions of 5 g or more per square millimeter of the preform's cross-sectional area (e.g., 7 g or more, 10 g or more, 15 g or more, 20 g or more, 25 g or more, 30 g or more) are applied to the preform.

An important component of the process of producing fibers according to the flow chart in FIG. 2 is the selection of materials—including conductors, insulators, non-centrosymmetric materials—that can be co-drawn, and can maintain both structural integrity and chemical composition at the fiber draw temperature. As used herein, maintaining structural integrity refers to a fiber material that retains its physical properties when it is drawn from the preform into a fiber. Thus, for example, while the material may elongate during the drawing process, when the material cools and solidifies in the drawn fiber, the material's bulk properties (e.g., brittleness, elasticity, tensile strength, conductivity, dielectric strength, index of refraction) are the same in the fiber as they were in the preform; the material suffers no change or degradation in its mechanical, optical, or electronic properties as a result of the drawing process.

Further, maintaining chemical composition refers to a fiber material that retains its empirical chemical compositional formula during the drawing process. During drawing, the material may change its physical structure—it may undergo phase transitions, for example—but the elemental composition of the material in the drawn fiber is the same as the elemental composition of the material in the preform.

The selected materials support a matching flow rate, and do not undergo either axial or cross-sectional capillary break-up during drawing. To ensure that suitable flow rates are achieved and break-up of fiber materials during drawing is avoided, materials with certain viscosity properties are selected for use. In particular, materials are selected such that viscous forces within the materials oppose interface energy-driven capillary break-up mechanisms, and at the same time permit the materials to be drawn at suitable rates. Referring to FIG. 1, the material that forms the first conductor in regions 104 and 106 is typically a material with a sufficiently high viscosity at the fiber drawing temperature so that capillary break-up is avoided. In this manner, the first conductor maintains a large surface area of contact with the non-centrosymmetric material in region 102 in the drawn fiber. In contrast, regions 110, 112, 114, and 116 can have significantly smaller cross-sectional areas than regions 104 and 106, closer in aspect ratio to the cross-sectional profile of a filament. Accordingly, the material that forms the second conductor in regions 110, 112, 114, and 116 can be a lower viscosity—but higher conductivity—material that imparts high electrical conductivity along the length of the drawn fiber. Because the cross-sectional area of regions 110, 112, 114, and 116 is smaller, the increased tendency of the second material in these regions to form filament-like structures upon drawing (relative to the first material in regions 104 and 106) does not impair the functioning of fiber 100. To the contrary, the materials in the first and second regions of the drawn fiber together form electrodes that provide both high surface areas of contact with the non-centrosymmetric material, and high electrical conductivity extending along the length of the fiber.

To provide stability during drawing, at least one of the materials assembled in the preform is chosen to support the draw tension and maintain continuous and controllable deformation during the drawing process. Typically, the insulator is selected to perform this function, although more generally any one or more of the materials in the preform can function in this manner.

Further, the materials assembled in the preform (and present in the drawn fiber) flow at a common draw temperature. While the draw temperature can be selected based on the nature of the materials, the materials should flow at whichever draw temperature is selected. To ensure that each of the materials flow, each material is selected such that it has a viscosity of $10^7$ Poise or less (e.g., $10^6$ Poise or less, $10^5$ Poise or less) at the common fiber draw temperature.

Typically, the selected materials also exhibit good adhesion and/or wetting properties in the viscous and solid states. Further, the materials are typically selected such that their thermal expansion coefficients are relatively closely matched to prevent cracking and delamination when the drawn fibers are cooled.

A variety of different materials can be used for each of the components of the preforms and fibers disclosed herein. In some embodiments, the insulator can include a polymeric material; the polymeric material can, in certain embodiments, have a relatively high glass transition temperature (e.g., a glass transition temperature of 200° C. or more). An exemplary but inexhaustive list of materials that can be used as insulators includes polyimide materials, polysulfone materials, polycarbonate materials, polymethacrylate materials, polyester materials, polyacrylate materials, polyether sulfone materials, cyclic olefin materials, fluorinated polymer materials, and thermoplastic materials. Other materials that can be used to form the insulator include high temperature insulating materials such as silica and silica glass.

Moreover, as will be discussed in greater detail later, the insulator can have a variety of different shapes according to the shape of the drawn fibers. In FIG. 1A, the insulator in region 108 is in the form of a tube (e.g., a polymeric tube). More generally, the insulator can assume other forms as well, including being shaped as a rod and as a planar layer in certain embodiments.

Various components can also be present in the first conducting material in regions 104 and 106. In general, the first conducting material is formed as a composite that includes a host material and a plurality of conducting particles within the host material. Suitable host materials include, for example, polycarbonate materials, polyethylene materials, acrylonitrile-butadiene-styrene copolymer materials, acetal copolymer materials, polypropylene materials, poly(vinylidene fluoride) materials, and polyetherimide materials. Suitable conducting particles include, for example, carbon particles, carbon fibers, carbon nanotubes, and stainless steel fibers.

The non-centrosymmetric material in active region 102 can include one or more components selected with a view to the considerations discussed above. In certain embodiments, the non-centrosymmetric material includes a crystalline material. In some embodiments, the non-centrosymmetric material includes a piezoelectric material. Piezoelectric materials, as discussed above, convert mechanical stress or strain into an electrical potential difference at the surface of the material via the piezoelectric effect. Piezoelectric materials also exhibit the reverse piezoelectric effect in which a mechanical perturbation is induced in the material when a time-varying electric field is applied to the material. In certain embodiments, the non-centrosymmetric material can include one or more ferroelectric materials. Ferroelectric materials, in addition to being piezoelectric, are also pyroelectric by virtue of their symmetry. Further, ferroelectric materials have a macroscopic polarization that can typically be reversed by an applied electric field.

Exemplary non-centrosymmetric materials that can be used in the fibers disclosed herein include polymers and copolymers. In particular, polymer and copolymer materials can include, but are not limited to, poly(vinylidene fluoride) materials, copolymers of vinylidene fluoride and trifluoroethylene, polyvinyl chloride materials, copolymers of vinyl acetate and vinylidene cyanide, nylon polymer materials, nylon copolymer materials, polyacrylonitrile materials, and a variety of high temperature ceramic materials such as lead zirconate titanate, quartz, barium titanate, and cadmium sulfide. In some embodiments, combinations of two or more materials can be used to form the non-centrosymmetric material. For example, the non-centrosymmetric material can include piezoelectric particulates (e.g., any of the piezoelectric materials disclosed herein) embedded in a matrix material (e.g., any of the materials disclosed herein that are suitable hosts for particulates).

Additional exemplary non-centrosymmetric materials that can be used in fibers include berlinite ($AlPO_4$); cane sugar; Rochelle salt; topaz; tourmaline-group minerals; biological materials such as bone and collagen, tendon, silk, wood, enamel, and dentin; gallium orthophosphate ($GaPO_4$); langasite ($La_3Ga_5SiO_{14}$); ceramics with perovskite or tungsten-bronze structures; lead titanate; potassium niobate; lithium niobate; lithium tantalate; sodium tungstate; $Ba_2NaNb_5O_5$; $Pb_2KNb_5O_{15}$; sodium potassium niobate; bismuth ferrite; and sodium niobate.

Certain materials that are used in fibers may have multiple phases, some of which are non-centrosymmetric and other which are centrosymmetric. By controlling the fiber drawing conditions and/or by post-processing after the fiber drawing process is complete, such materials can be placed in their non-centrosymmetric (e.g., piezoelectric and/or ferroelectric phases) in the fibers. For example, certain centrosymmetric materials, when heated to a molten phase at a certain drawing temperature, drawn under tension, and/or cooled from the melt at particular rates, form non-centrosymmetric crystalline phases upon solidification.

The second conductor in each of regions 110, 112, 114, and 116 typically contacts the first conductor in one of regions 104 and 106 to form electrodes positioned on opposite sides of active region 102. The first and second conductors are in contact along the common length of fiber 100 (e.g., along the length over which the insulator and the non-centrosymmetric material extend as well). As such, the second conductor is typically formed of one or more highly conductive materials that are co-drawable with the other fiber materials at the common fiber draw temperature, and maintain both structural integrity and chemical composition at the draw temperature. Exemplary materials that can be used to form the second conductor include metals and alloys. For example, the metals and/or alloys used to form the second conductor can include one or more of bismuth, lead, tin, indium, cadmium, gallium, copper, aluminum, silver, gold, zinc.

During preform drawing, capillary break-up of a conductor due to flow instabilities caused by the drawing process can lead to a fiber with filaments of conducting material rather than a layer. Such filaments typically have surface areas of contact with other fiber materials that are significantly smaller than the large areas of contact afforded by the first conducting material in fiber 100, resulting in less efficient interconversion of electrical energy and mechanical energy in drawn fibers. Moreover, at elevated drawing temperatures, the filaments can mix with other fiber materials, resulting in inhomogeneous cross-sectional profiles (e.g., layer thickness nonuniformity in either the lateral or longitudinal directions) in the drawn fibers. This inhomogeneity can preclude proper activation (e.g., poling) of the fibers, as discussed later.

In embodiments disclosed herein, capillary break-up during preform drawing can be avoided by selecting the first conducting material such that it retains sufficiently high viscosity so that capillaries do not form during drawing. Typically, for example, to ensure that capillary break-up does not occur, the first conducting material has a viscosity of $10^2$ Poise or more (e.g., $10^3$ Poise or more, $10^4$ Poise or more) at the common fiber draw temperature. Because conducting materials that are sufficiently viscous may have less than preferred conductivities, especially for carrying current over an extended length of the fiber, the second conducting material can be used. For example, the second conducting material can be metal that contacts the first conducting material along the full length of the fiber. Moreover, the cross-sectional area of this second conducting material can already be small (e.g., like that of a filament), so that capillary break-up of the second conducting material during drawing is moot.

Regions 110, 112, 114, and 116 which include the second conducting material can generally have a variety of different shapes. In FIG. 1A, each of these regions is implemented as an elongated strand that extends substantially along the length of fiber 100 such that the cross-sectional dimensions of each region are significantly smaller than the length of each region. In some embodiments, however, some or all of the regions that include the second conducting material can be implemented as one or more layers in a planar layer stack.

In general, the fiber performs that are formed according to the methods disclosed herein have lengths of about 50 cm or less (e.g., 40 cm or less, 30 cm or less, 20 cm or less, 10 cm or less, 5 cm or less, 1 cm or less, 0.5 cm or less). From such a starting length, a fiber preform can be drawn to a significantly extended length to form fiber 100. For example, the drawn fiber can have a length that is 100 times or more (e.g., 500 times or more, 1000 times or more, 5000 times or more, 10000 times or more) longer than the length of the preform. In some embodiments, the length L of fiber 100 is 10 cm or more (e.g., 50 cm or more, 1 meter or more, 5 meters or more, 10 meters or more, 20 meters or more, 30 meters or more, 50 meters or more, 100 meters or more, 500 meters or more, 1000 meters or more, 10000 meters or more, 50000 meters or more).

The drawn fiber can also have a maximum cross-sectional dimension that is significantly smaller than the maximum cross-sectional dimension of the fiber preform. For example, in certain embodiments, the drawn fiber has a maximum cross-sectional dimension of 2 mm or less (e.g., 1.5 mm or less, 1 mm or less, 0.5 mm or less, 0.25 mm or less, 0.1 mm or less, 50 microns or less, 10 microns or less, 5 microns or less). In some embodiments, a ratio of the maximum cross-sectional dimension of the fiber preform to the maximum cross-sectional dimension of the drawn fiber is 10 or more (e.g., $10^2$ or more, $10^3$ or more, $10^4$ or more). Fiber 100 has a fiber axis along which its length L is measured, and a maximum cross-sectional dimension measured along a direction orthogonal to the fiber axis. In certain embodiments, a ratio of the fiber length L to the fiber's maximum cross-sectional dimension is $10^3$ or more (e.g., $10^4$ or more, $10^5$ or more, $10^6$ or more, $10^9$ or more, $10^{12}$ or more).

Following drawing of the preform to form fiber 100, each of the regions that include the first conductor in fiber 100 has a maximum cross-sectional length measured along an outer surface of the region and a thickness measured in a direction orthogonal to the outer surface. For example, referring to FIG. 1A, region 104 has a maximum cross-sectional length that corresponds to a circumference of the outer surface of region 104 (e.g., the surface of the first conductor in region 104 that contacts the non-centrosymmetric material in active region 102), and a thickness measured in a radial direction perpendicular to the outer surface of the first conductor in region 104. In some embodiments, a ratio of the maximum cross-sectional length to the thickness for a region with the first conductor is 3 or more (e.g., 5 or more, 10 or more, 20 or more, 50 or more, 75 or more, 100 or more, $10^3$ or more, $10^4$ or more, $10^5$ or more, $10^6$ or more). By maintaining a large ratio of maximum cross-sectional length to thickness, the regions with the first conductor have a large surface area, thereby facilitating efficient piezoelectric operation of fiber 100.

The non-centrosymmetric material, the first and second conductors, and the insulator can also be selected according to their electrical properties. Selecting conductors with relatively low resistivity can yield fibers that efficiently interconvert electrical and mechanical energy. In certain embodiments, the conductors, which are in electrical contact with the non-centrosymmetric material, can have an electrical resistivity of $10^5$ ohm·m or less (e.g., $10^4$ ohm·m or less, $10^3$ ohm·m or less, $10^2$ ohm·m or less, 10 ohm·m or less). As explained above, two different conductors can be used to achieve, on the one hand, large surface area contact with the piezoelectric material (by using a viscous conductor), and, on the other hand, high conductivity over the length of the fiber (by using metal filament-like regions in electrical contact with the large surface are viscous conductor). Selecting insulators with relatively high resistivity can help to prevent electrical discharge in fibers during operation and/or activation. In some embodiments, the insulator can have an electrical resistivity of $10^8$ ohm·m or more (e.g., $10^9$ ohm·m or more, $10^{10}$ ohm·m or more, $10^{11}$ ohm·m or more, $10^{12}$ ohm·m or more).

Prevention of dielectric breakdown in fiber 100 can be assisted by using large area conductors, which reduces the need for large driving voltages to be applied to the non-centrosymmetric material in active region 102 of fiber 100. Further, the insulator can be selected to ensure that arcing and other dielectric breakdown events do not occur within fiber 100, particularly during activation (e.g., poling) of the fiber. In some embodiments, for example, the insulator has a dielectric strength of 10 V or more per micron of thickness (e.g., 15 V/µm or more, 20 V/µm or more, 30 V/µm or more, 40 V/µm or more, 50 V/µm or more, 75 V/µm or more, 100 V/µm or more).

In some embodiments, the non-centrosymmetric material is selected for its dielectric properties. In particular, in some embodiments, the non-centrosymmetric material can sustain a field of 3 MV/m or more (e.g., 4 MV/m or more, 5 MV/m or more, 7 MV/m or more, 10 MV/m or more, 15 MV/m or more, 20 MV/m or more, 30 MV/m or more, 50 MV/m or more) when an electrical potential difference is applied between the first electrode (e.g., regions 104, 114, and 116) and the second electrode (e.g., regions 106, 110, and 112) in fiber 100.

Exemplary fibers were constructed according to the criteria discussed above. Carbon-doped polycarbonate and polyethylene were used as the first conductor in the fabricated fibers, and polycarbonate and polysulfone materials were used as the insulator. The second conductor was formed from alloys of bismuth and tin, and from indium metal, and was implemented in the form of metallic strands that extended substantially along the entire length of the drawn fibers.

Piezoelectric poly(vinylidene fluoride) copolymers were used as the non-centrosymmetric material. Poly(vinylidene fluoride) (PVDF) and its copolymers are commercially available piezoelectric polymers and have high piezoelectricity when poled. However, piezoelectricity only occurs in two phases of PVDF; moreover, direct cooling of molten PVDF typically yields α-PVDF, which is not a piezoelectric phase. To fabricate a piezoelectric non-centrosymmetric material, a PVDF copolymer was prepared that consisted of poly(vinylidene fluoride-trifluoroethylene) (P(VDF-TrFE)). The P(VDF-TrFE) copolymer spontaneously solidified into a piezoelectric and ferroelectric β-phase when cooled from molten form.

Returning to the flow chart of FIG. 2, following cooling of the drawn fiber (which causes the material in active region 102 to crystallize in a non-centrosymmetric phase), in optional step 208 the non-centrosymmetric material in the drawn fiber is activated to achieve a piezoelectric response (or to enhance its existing piezoelectricity). Activation of the material typically occurs by high-field poling. For example, a DC voltage can be applied to the electrodes of the fiber, establishing an electric field of magnitude at least 10 V or more (e.g., 15 V or more, 20 V or more, 30 V or more, 40 V or more, 50 V or more, 75 V or more, 100 V or more, 150 V or more) per μm of thickness of the non-centrosymmetric material. The voltage can be applied for 1 minute or more (e.g., 2 minutes or more, 3 minutes or more, 5 minutes or more, 7 minutes or more, 10 minutes or more, 15 minutes or more, 20 minutes or more, 30 minutes or more). During this period of time, the DC electric field aligns the electric dipoles of individual domains in the non-centrosymmetric material from an initial random or pseudo-random orientation, achieving a macroscopic polarization in the non-centrosymmetric material.

In some embodiments, high-field poling of the non-centrosymmetric material can be preceded by a thermal annealing step to increase the crystallinity of the non-centrosymmetric material, further increasing the piezoelectricity of the material following poling. Thermal annealing can occur at a temperature of 100° C. or more (e.g., 105° C. or more, 110° C. or more, 115° C. or more, 120° C. or more, 125° C. or more) and/or 150° C. or less (e.g., 145° C. or less, 140° C. or less, 135° C. or less, 130° C. or less). In some embodiments, thermal annealing is performed for a period of 1 hour or more (e.g., 1.5 hours or more, 2 hours or more, 3 hours or more, 4 hours or more, 5 hours or more).

Following activation of the non-centrosymmetric material, the fiber is ready for use and the process shown in flow chart 200 ends at step 210. Additional methods and systems for fabricating preforms and drawing fibers are disclosed, for example, in U.S. Pat. No. 7,295,734, and in U.S. Patent Application Publication No. US 2008/0087047.

Returning again to FIG. 1A, fiber 100 has cylindrical symmetry about the fiber axis, and the outer perimeter of fiber 100 has a circular shape. In general, however, the fibers disclosed herein can have a wide variety of different shapes. In some embodiments, the fibers can have a symmetric cross-sectional shape as shown in FIG. 1A. Alternatively, in certain embodiments, the fibers can have an asymmetric or irregular cross-sectional shapes.

Figure 3:
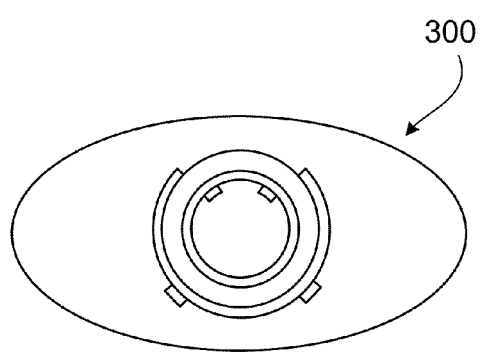
FIG. 3 is a cross-sectional view of a fiber with an elliptical cross-sectional shape.
Figure 4:
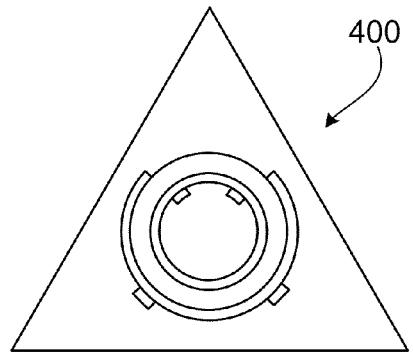
FIG. 4 is a cross-sectional view of a fiber with a triangular cross-sectional shape.
Figure 5:
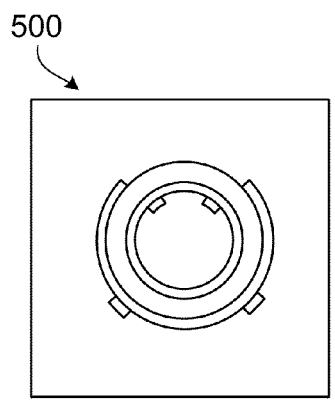
FIG. 5 is a cross-sectional view of a fiber with a square cross-sectional shape.
Figure 6:
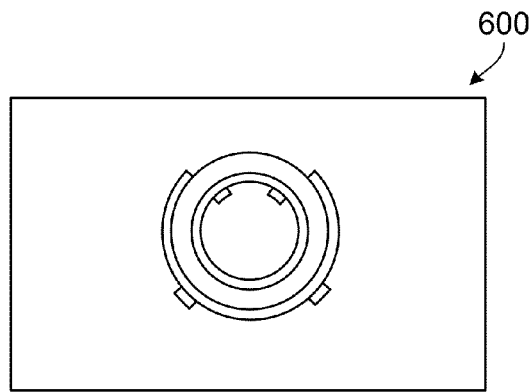
FIG. 6 is a cross-sectional view of a fiber with a rectangular cross-sectional shape.
Figure 7:
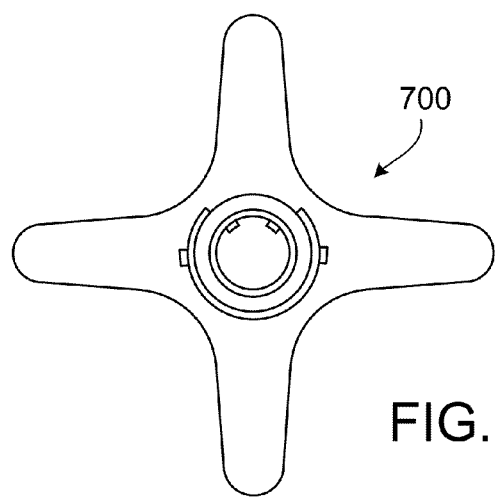
FIG. 7 is a cross-sectional view of a fiber with a symmetrical cross-sectional shape.

Further, in some embodiments, the fibers disclosed herein can have an outer perimeter that is symmetric but not circular. For example, the shape of the outer perimeter of the fibers can be elliptical (as shown in FIG. 3 for fiber 300), triangular (as shown in FIG. 4 for fiber 400), square (as shown in FIG. 5 for fiber 500), and rectangular (as shown in FIG. 6 for fiber 600). More generally, the shape of the outer perimeter of the fibers disclosed herein can be polygonal and can correspond to an n-sided polygon. The shape of the outer perimeter of the fibers can also correspond to symmetric shapes that are not polygonal. A cross-sectional view of an embodiment of one such fiber 700 is shown in FIG. 7. Fibers with many different shapes can be formed by constructing suitable preforms.

Figure 8:
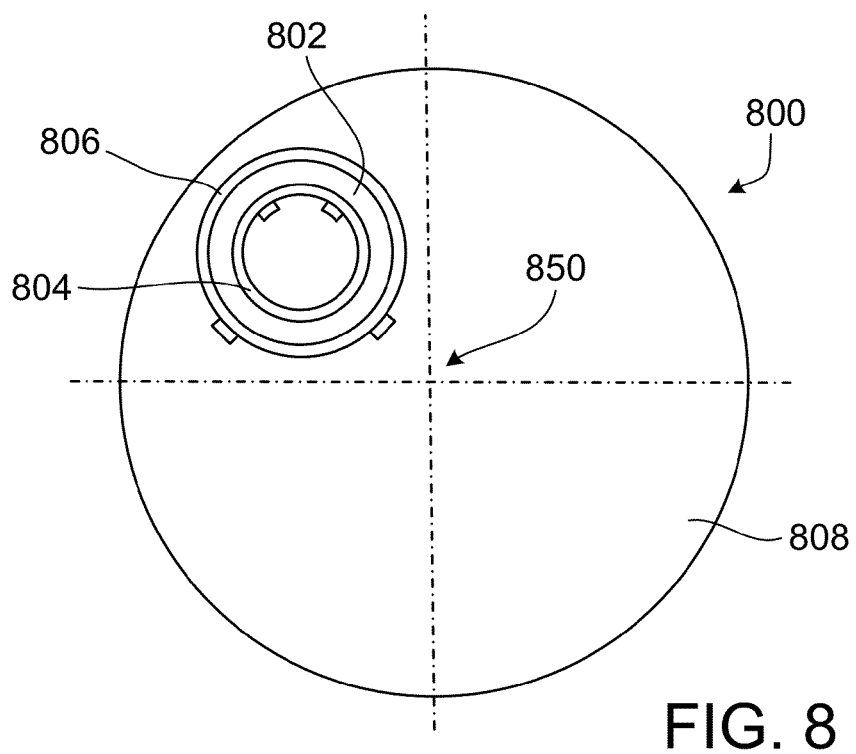
FIG. 8 is a cross-sectional view of a fiber with a non-centrosymmetric material in an offset position relative to a central axis of the fiber.

In some embodiments, non-centrosymmetric material, the first conductor, and the insulator are symmetrically oriented about the fiber axis. More generally, however, some or all of these materials can be positioned in regions that are oriented asymmetrically with respect to an axis of fiber 100. FIG. 8 shows a cross-sectional view of an embodiment of a fiber 800 that includes an insulator positioned in a region 808. A fiber axis 850 is oriented at the center of region 808 and extends along a length of the fiber, perpendicular to the view in FIG. 8. Fiber 800 also includes a first conductor positioned in regions 804 and 806, and a non-centrosymmetric material positioned in active region 802. However, while the first conductor in regions 804 and 806 is positioned symmetrically with respect to the non-centrosymmetric material in region 802, regions 802, 804, and 806 are offset from fiber axis 850. In general, regions 802, 804, and 806 can occupy any of a variety of different offset positions relative to fiber axis 850, provided that the structural integrity of each of the fiber materials is maintained during drawing.

Figure 9:
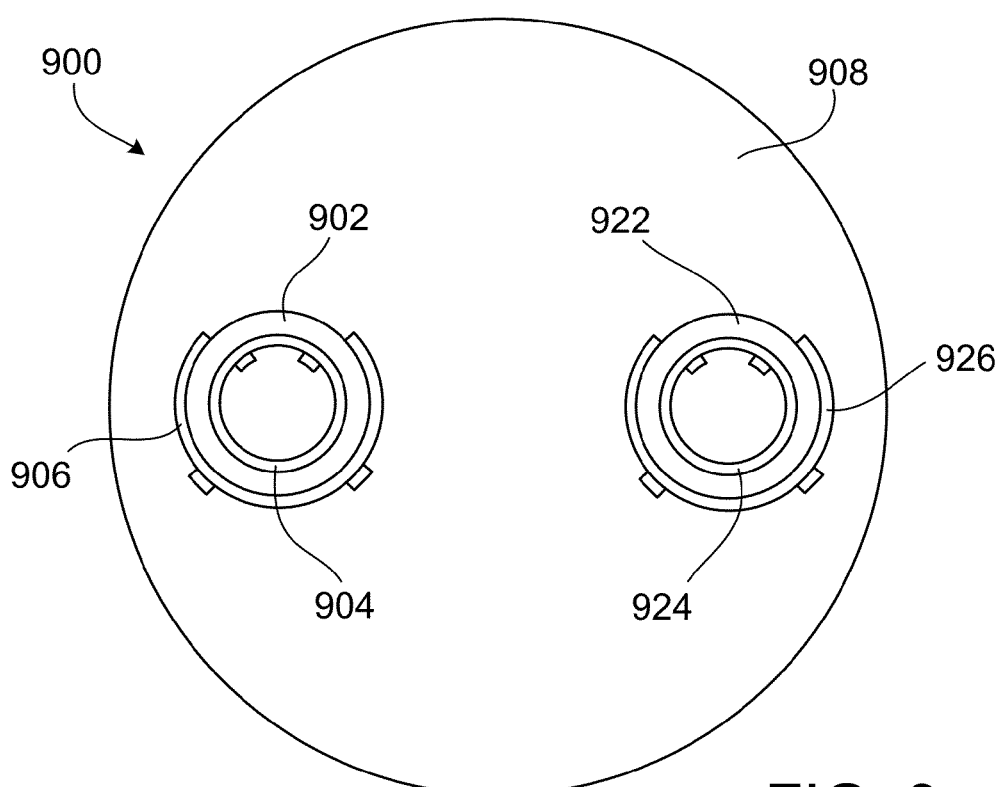
FIG. 9 is a cross-sectional view of a fiber with more than one non-centrosymmetric material.

In certain embodiments, more than one non-centrosymmetric material and corresponding conductors can be present in a single fiber. FIG. 9 shows a cross-sectional view of an embodiment of a fiber 900 that includes an insulator in a region 908, a non-centrosymmetric material in a region 902, and a first conductor in regions 904 and 906, surrounding region 902. Fiber 900 also includes the non-centrosymmetric material in a region 922, and regions 924 and 926 which also include the first conductor, and surround region 922. Both regions 902 and 922 in fiber 900 are implemented as tube-shaped regions. The outer perimeter of each tube of non-centrosymmetric material is a closed loop that does not contain the center of the cross-section of fiber 900.

Although FIG. 9 shows a fiber with two regions that include the non-centrosymmetric material and a pair of regions of the first conductor positioned on opposite sides of each of regions 902 and 922, more generally any number of regions with one or more non-centrosymmetric materials and/or one or more conductors can be included in the fibers disclosed herein, subject to geometrical and structural material constraints during fiber drawing. The multiple regions can be symmetrically positioned with respect to fiber axis 950, as shown in FIG. 9, or asymmetrically positioned with respect to the fiber axis.

Figure 10:
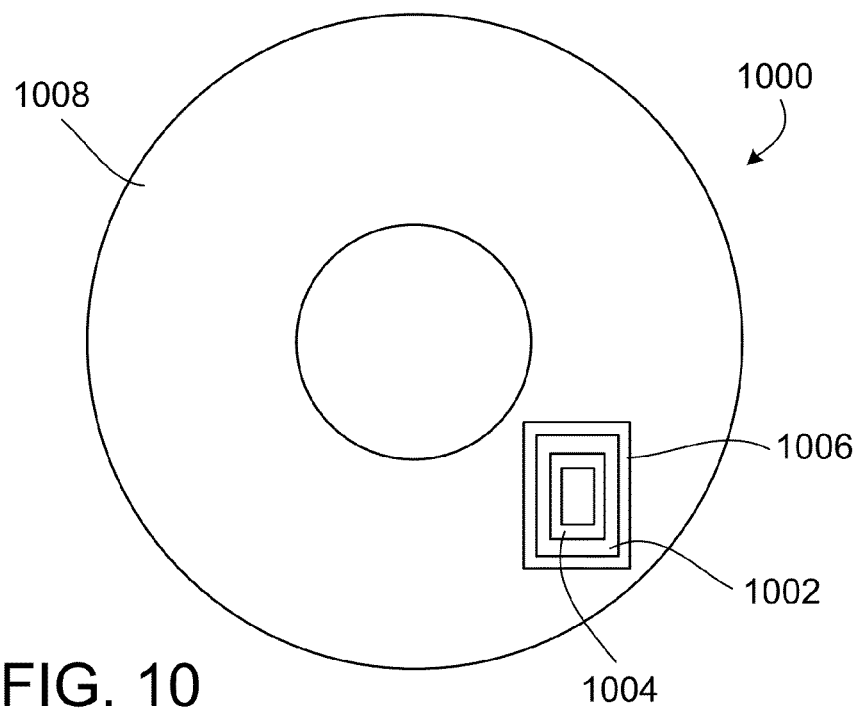
FIG. 10 is a cross-sectional view of a fiber with a non-centrosymmetric material that has symmetry different from the symmetry of the fiber surfaces.

Further, in some embodiments, certain fiber elements can have shapes that do not share the symmetry of either or both of the fiber inner perimeter and the fiber outer perimeter. For example, FIG. 10 shows a fiber 1000 that includes an insulating material positioned in a region 1008. The inner surface of region 1008 forms the inner surface of fiber 1000, and the outer surface of region 1008 forms the outer surface of fiber 1000. The cross-sectional symmetry of both the inner and outer surfaces of fiber 1000 is circular ($C_\infty$ about the fiber axis). Fiber 1000 also includes a non-centrosymmetric material positioned in region 1002, and a first conductor positioned in regions 1004 and 1006. Regions 1002, 1004, and 1006 are displaced from the geometric cross-sectional center of fiber 1000. Further, as shown in FIG. 10, regions 1002, 1004, and 1006 have square cross-sectional shapes with $C_4$ symmetry, in contrast to the circular cross-sectional shapes of the inner and outer surfaces of fiber 1000.

In general, the various regions of fiber 1000—including the regions that include the non-centrosymmetric material, the first and second conductors, and the insulator—can have a variety of different cross-sectional shapes, including circular, triangular, square, rectangular, polygonal, and curved. The cross-sectional shapes can be regular or irregular, and symmetrical or asymmetrical. Further, as shown in FIG. 10, the cross-sectional symmetry of any of the regions in fiber 1000 can be the same as, or different from, the symmetry of the inner and/or outer surfaces of fiber 1000.

Returning again to FIG. 1A, regions 110, 112, 114, and 116 are generally used to form external electrical contacts to regions 104 and 106 and the first conductor therein. In FIG. 1A, the second conductor in two regions 110 and 112 contacts the first conductor in region 106, and the second conductor in two regions 114 and 116 contacts the first conductor in region 104. Electrical signals can therefore be coupled into region 104 through regions 114 and 116, and electrical signals can be coupled into region 106 through regions 110 and 112.

Although in FIG. 1A the first conductor in each of regions 104 and 106 has two associated regions of the second conductor, more generally each region of the first conductor can have any number of associated regions of the second conductor, including none at all. Further, the regions of the second conductor associated with each region of the first conductor can be arranged in any geometry relative to the regions of the first conductor, subject to geometrical and structural material constraints in the fiber. Although regions 110, 112, 114, and 116 are depicted in FIG. 1A as having rectangular cross-sectional shapes, more generally any one or more of these regions can have any regular or irregular geometrical shape in cross-section.

Figure 11:
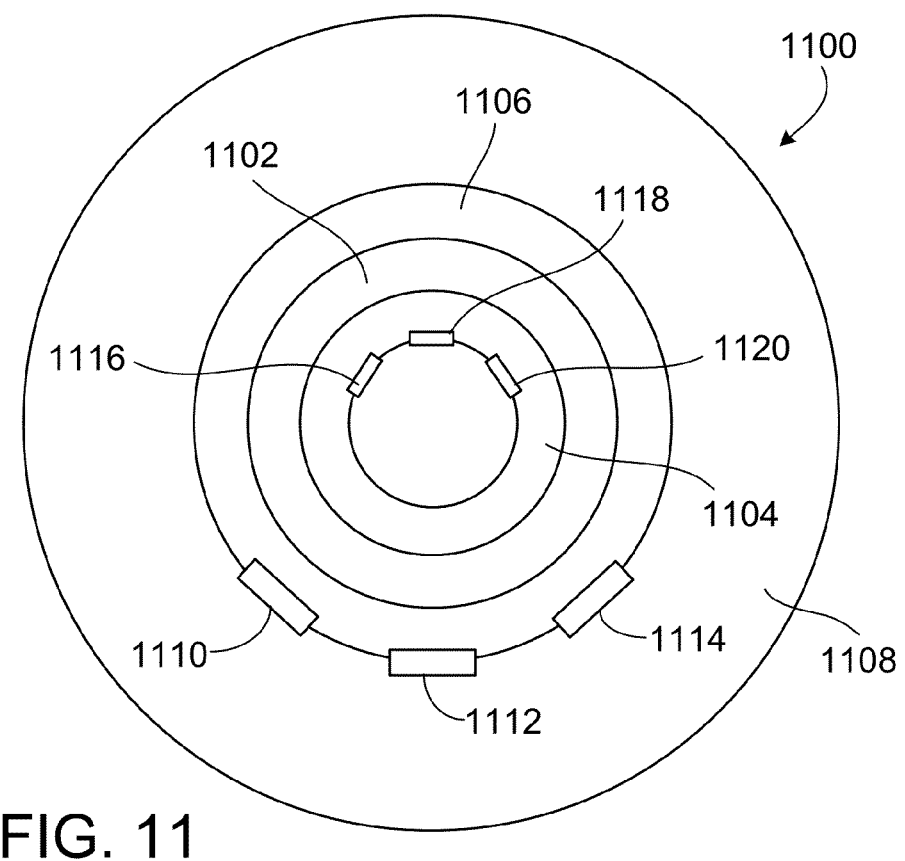
FIG. 11 is a cross-sectional view of a fiber with electrodes positioned in grooves formed in surfaces of conductive materials.

As shown in FIG. 1A, regions 110, 112, 114, and 116 are positioned so that they contact a surface of one of regions 104 and 106, thereby ensuring that the first and second conductors are in contact at each interface. In certain embodiments, the second conductor can be positioned in grooves formed in the first conductor or in the insulator. The grooves permit the second conductor to be stabilized in position prior to drawing, thereby ensuring that the positions of regions of the second conductor remain approximately constant relative to other fiber features along a length of the drawn fiber. FIG. 11 shows a cross-sectional view of a fiber 1100 that includes a non-centrosymmetric material in a region 1102, a first conductor in a region 1104 with three associated regions 1116, 1118, and 1120 of a second conductor, the first conductor also in a region 1106 with three associated electrodes 1110, 1112, and 1114, and an insulating material 1108. The second conductor in regions 1116, 1118, and 1120 is positioned in grooves formed in the inner surface of region 1104. Similarly, the second conductor in regions 1110, 1112, and 1114 is positioned in grooves formed in the outer surface of region 1106.

In some embodiments, the second conductor can be applied to a surface of the first conductor using a liquid polymer adhesive. For example, regions 1110, 1112, and 1114 of the second conductor can be applied directly to the surface of region 1106 of the first conductor by first applying a liquid polymer adhesive solution to the surface of region 1106, and then positioning the second conductor so that it contacts at least a portion of the applied liquid polymer adhesive.

In some embodiments, the regions of the non-centrosymmetric material and the first conductor form concentric layers in the fiber. The region of the insulator can also form a layer that is concentric with the regions of the non-centrosymmetric material and the first conductor. For example, referring again to FIG. 1A, the first conductor in regions 104 and 106, the non-centrosymmetric material in region 102, the second conductor in regions 110, 112, 114, and 116, and the insulator in region 108 form concentric layers of increasing circumference moving in a direction outward from the cross-sectional center of fiber 100 toward its outer surface.

Figure 12A:
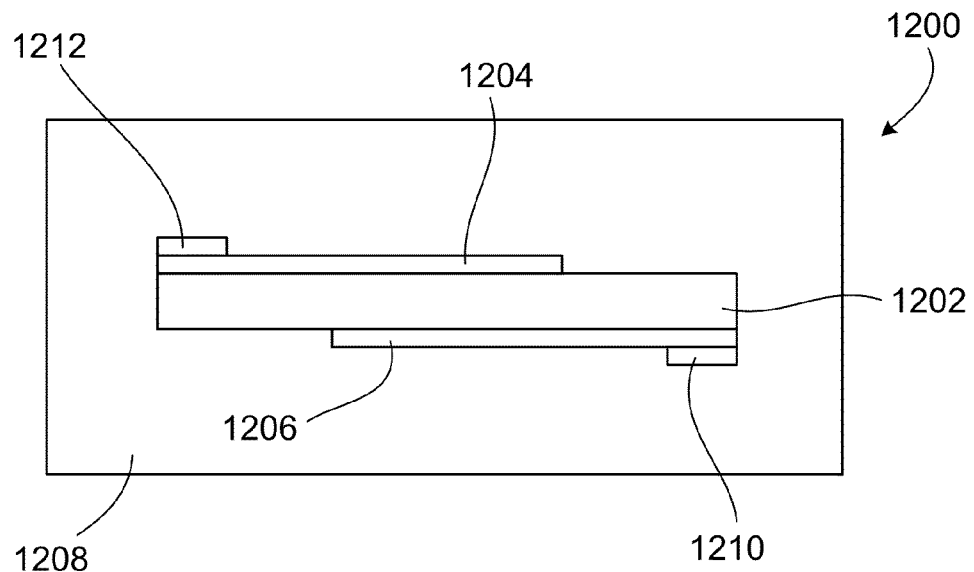
FIG. 12A is a cross-sectional view of a fiber that includes a planar material stack.
Figure 12B:
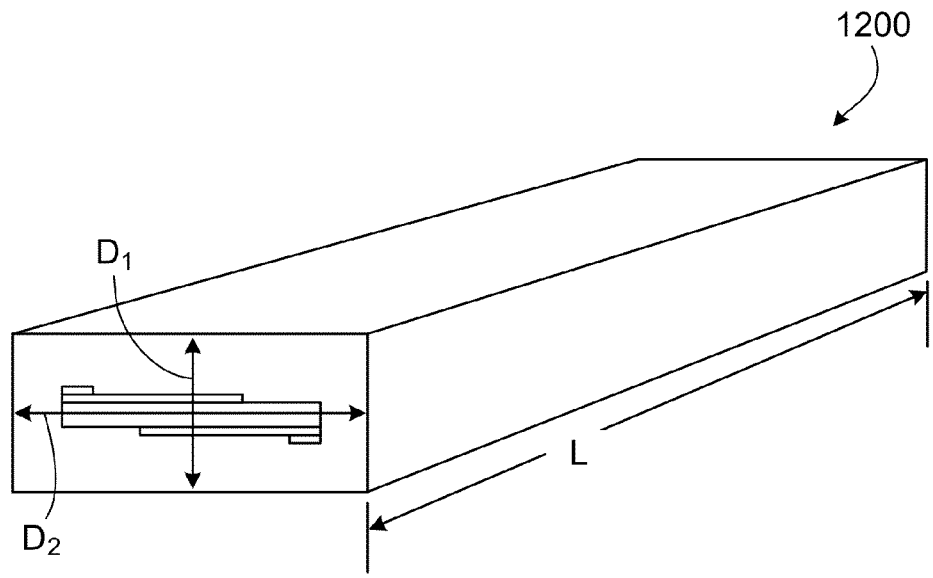
FIG. 12B is a perspective view of the fiber of FIG. 12A.

The materials can also be arranged in other geometries. FIG. 12A shows a cross-sectional view of a fiber 1200 with a rectangular cross-sectional shape, and FIG. 12B shows a perspective view of the same fiber. Fiber 1200 includes a layer of non-centrosymmetric material in region 1202, a first conductor in regions 1204 and 1206, and a second conductor in regions 1212 and 1210 that contacts the first conductor in regions 1204 and 1206, respectively. Region 1208 includes the insulator, and encloses regions 1202, 1204, 1206, 1210, and 1212. Fiber 1200 extends for a length L along a fiber axis, and has cross-sectional dimensions $D_1$ and $D_2$ in directions orthogonal to the fiber axis.

In FIGS. 12A and 12B, due to the configuration and geometry of regions 1202, 1204, and 1206, the non-centrosymmetric material, the first conductor (2 layers) and the insulator form a planar layer stack. In the embodiment shown, region 1208 encloses the non-centrosymmetric material in region 1202 and the first conductor in regions 1204 and 1206. In some embodiments, however, the insulator in region 1208 is applied to only certain surfaces of the planar layer stack. For example, the insulator in region 1208 can be applied only to the upper surface of region 1204 and to the lower surface of region 1206, thereby exposing side surfaces of the internal layers of the layer stack. Electrical contacts, additional insulators and/or conductors, and other materials or devices can be applied to the exposed layer surfaces.

In certain embodiments, the cross-sectional shapes of the regions of the conductors and/or the regions of the non-centrosymmetric material can be further chosen to improve the efficiency with which the non-centrosymmetric material converts electrical energy to acoustic waveforms (and/or converts mechanical perturbations to electrical signals). For example, regions of the first conductor can have a cross-sectional shape that features a plurality of electrically connected planar surfaces. When each region of the first conductor is shaped in this manner, the regions of the first conductor can be positioned such that they form a "folded" fiber with a stack of interdigitated planar layers at alternating potentials.

Figure 13:
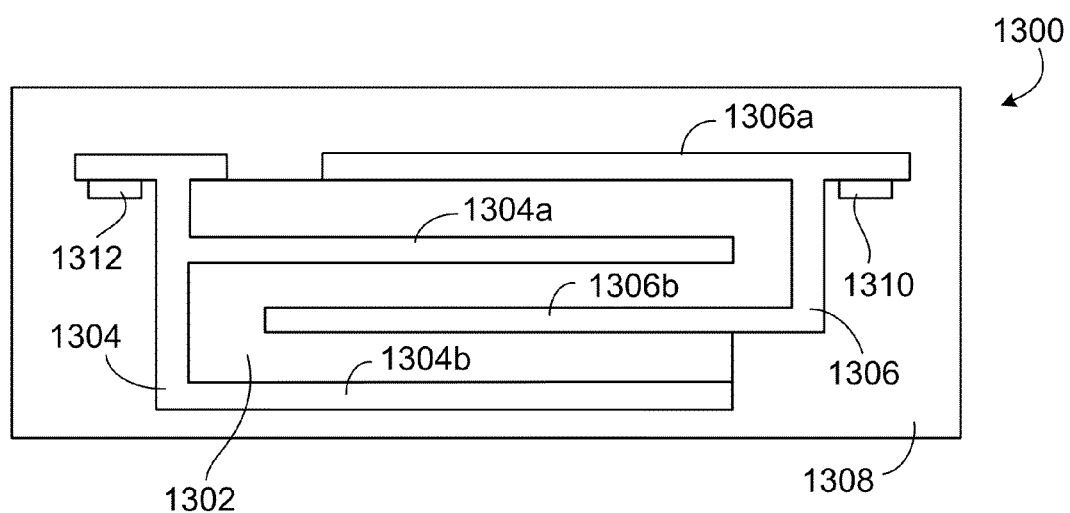
FIG. 13 is a cross-sectional view of a fiber with a folded internal structure.

FIG. 13 shows a cross-sectional view of an exemplary fiber 1300 that includes regions of a first conductor with multiple planar layers. Fiber 1300 features a region 1304 that includes a first conductor with two planar layers 1304a and 1304b, and a region 1306 that also includes the first conductor with two planar layers 1306a and 1306b. The two planar layers of the first conductor in each region are integrally connected to form a single continuous conductor. Regions 1304 and 1306 are arranged such that the planar layers of each region form a stack in which planar layers from the two regions alternate, but do not touch one another. A non-centrosymmetric material is positioned in region 1302, in the spaces between the planar layers of regions 1304 and 1306. Regions 1310 and 1312 that include the second conductor contact regions 1306 and 1304, respectively, and permit an electrical potential to be applied to the first conductor in each of regions 1304 and 1306. Insulating material in region 1308 surrounds regions 1304 and 1306, region 1302, and regions 1310 and 1312.

Each portion of the non-centrosymmetric material in region 1302 in fiber 1300 can function as an acoustic transducer. For example, planar layers 1306a and 1304a of the first conductor in combination with the portion of the non-centrosymmetric material in region 1302 between these two layers functions as a transducer structure. Similarly, planar layers 1304a and 1306b of the first conductor in combination with the portion of the non-centrosymmetric material in region 1302 between these layers functions as another transducer. Because the layers of region 1304 are mutually electrically connected, and the layers of region 1306 are (separately) mutually electrically connected, the various portions of fiber 1300 that operate as transducers do not operate independently; rather, when an electrical potential is applied between regions 1304 and 1306 (e.g., via regions 1312 and 1310), acoustic waveforms can be generated in different portions of the non-centrosymmetric material in region 1302 at the same time.

By "folding" multiple non-centrosymmetric material regions in a single fiber, the voltage required to drive the transducer structure formed by the first conductor and the non-centrosymmetric material can be reduced relative to a single-layer acoustic transmitter. In an acoustic transmitter, the amount of electrical power converted into acoustic waveforms depends not only on the volume of the piezoelectric material, but also on the magnitude of the applied electric field. To apply a large field to a relatively small volume of material, the piezoelectric material should be relatively thin and have a large surface area. By folding the piezoelectric material regions in a fiber as shown in FIG. 13, a large-area piezoelectric material can be realized. Further, the multiple layers of the first conductor function as electrodes in FIG. 13 to apply fields throughout the volume of the piezoelectric material. As a result, both the conversion efficiency from electrical power to acoustic power, and the mechanical displacement of the piezoelectric material, are increased relative to non-folded fiber geometries.

When the fiber operates as an acoustic sensor or detector, its sensitivity is enhanced relative to a single-layer acoustic detector by using the folded geometry shown in FIG. 13. When operating as acoustic detectors, piezoelectric transducers generate surface charge in an amount proportional to the area of the piezoelectric material. Thus, by "folding" the piezoelectric material as in FIG. 13, up to hundreds of layers of piezoelectric material can be stacked, each layer having a thickness of a few microns and generating surface charges. As a result, the stacked piezoelectric material layers collectively function as a highly sensitive detector for acoustic waveforms that enter the material.

The folded fiber geometry shown in FIG. 13 therefore represents a significant improvement over more conventional stacked ceramic transducers. Stacked ceramic transducers have traditionally been limited in the number of stacked piezoelectric material layers that can be created and/or in the thickness of the layers. For example, typical microfabrication processes such as MEMs commonly permit only a few thin layers of piezoelectric material to be deposited on a chip due to the general difficulty of growing alternating layers of metals and piezoelectric ceramics. Bulk piezoelectric transducers can be mechanically stacked, but the large film thickness inherent in such devices makes large driving voltages (e.g., from tens to hundreds of volts) a requirement.

The present disclosure enables formation of thin-layer piezoelectric material stacks featuring tens or even hundreds of layers. The layer stacks can be assembled as preforms of macroscopic dimensions; as such, assembly of the selected fiber materials is generally relatively straightforward. Thermal drawing, described previously, is then used to scale down the layers of piezoelectric material to thicknesses of a few microns, while at the same time significantly increasing the surface area of the materials by drawing along the fiber axis. The drawing process thereby enables fabrication of fibers with internal multilayer, low-voltage, high sensitivity piezoelectric transducers.

Figure 14:
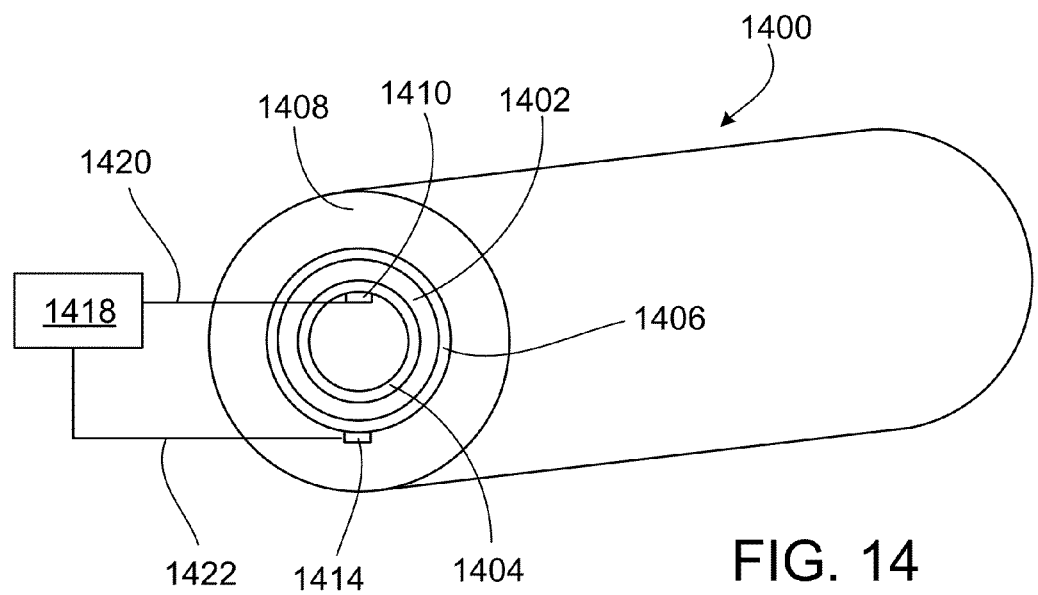
FIG. 14 is a perspective view of a fiber connected to an external control circuit.

Electrodes that contact the non-centrosymmetric material in the fibers disclosed herein can be externally connected to various devices, including power supplies, electronic controllers/circuits, and/or electronic processors. FIG. 14 shows an exemplary embodiment in which a fiber 1400 is connected to an electronic control circuit 1418. In FIG. 14, fiber 1400 includes a non-centrosymmetric material in region 1402, a first conductor in region 1404 with a second conductor in region 1410 contacting the first conductor in region 1404, the first conductor in region 1406 with the second conductor in region 1414 contacting the first conductor in region 1406, and an insulator in region 1408. Electronic control circuit 1418 is connected to region 1410 via control line 1420, and is connected to region 1414 via control line 1422.

In some embodiments, electronic control circuit 1418 is configured to direct electrical energy into fiber 1400 to generate an acoustic waveform in the fiber. That is, electronic control circuit is configured to apply a varying electrical potential between regions 1410 and 1414. The application of a varying electrical potential generates an acoustic waveform in non-centrosymmetric material in region 1402 via the reverse piezoelectric effect. The generated acoustic waveform can, in some embodiments, propagate along fiber 1400 within region 1402. In general, if the electric waveform has a particular frequency, the generated acoustic waveform has substantially the same frequency.

In certain embodiments, electronic control circuit 1418 is configured to receive an electrical signal from fiber 1400. For example, if an external event or perturbation introduces an acoustic waveform into the non-centrosymmetric material in region 1402 (e.g., an acoustic waveform that impinges upon the non-centrosymmetric material), the non-centrosymmetric material generates an electrical potential difference corresponding to the electrical waveform (e.g., a time-varying electric field) between regions 1404 and 1406 via the piezoelectric effect, in response to the acoustic waveform. Electronic control circuit 1418, by virtue of its connection to regions 1404 and 1406 (e.g., through control line 1420 connected to regions 1410 and 1404, and control line 1422 connected to regions 1414 and 1406), can receive the electrical signal from fiber 1400 that corresponds to the electric waveform as the acoustic waveform propagates in fiber 1400. In general, if the acoustic waveform has a particular frequency, the electric waveform has substantially the same frequency.

Based on the measured electrical signal, electronic control circuit 1418 can determine a property associated with the acoustic waveform in region 1402. In some embodiments, electronic control circuit 1418 can determine one or more of an amplitude of the acoustic waveform, a frequency of the acoustic waveform, and a propagation velocity of the acoustic waveform. Based on these waveform properties, electronic control circuit 1418 can also determine, for example, characteristics of other devices connected to fiber 1400 (e.g., devices that introduce the acoustic waveform into fiber 1400).

Although in FIG. 14 electrical connections to the electrodes of a fiber are made at the end of the fiber, such electrical connections can more generally be made at any position along the fiber where the electrodes are accessible. In particular, some fibers include regions along the length of the fiber where conductors internal to the fiber are exposed for purposes of electrically contacting the conductors. By virtue of their construction, certain conductors in such fibers can extend to an outer surface of the fiber.

Figure 15A:
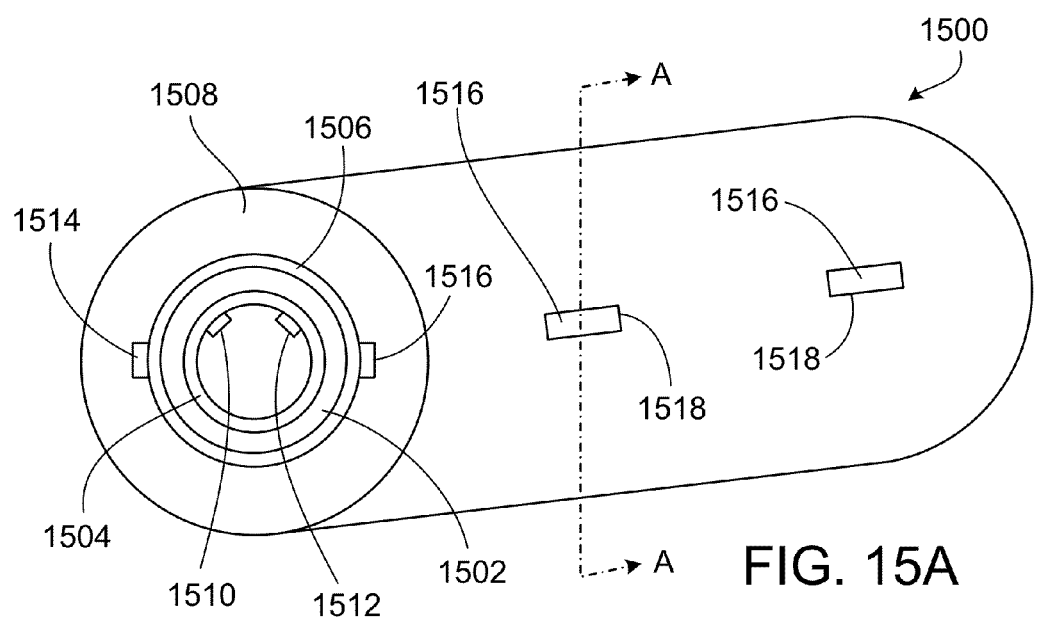
FIG. 15A is a perspective view of a fiber with recesses formed in its insulating material.

FIG. 15A shows a perspective view of an embodiment of a fiber 1500 that includes recesses that expose electrodes internal to the fiber. Fiber 1500 includes a non-centrosymmetric material in region 1502, a first conductor in regions 1504 and 1506, and an insulator in region 1508. Fiber 1500 also includes a second conductor in regions 1510, 1512, 1514, and 1516. The second conductor in regions 1510 and 1512 contacts the first conductor in region 1504; regions 1510 and 1512 can be electrically contacted at an end of fiber 1500, for example. The second conductor in regions 1514 and 1516 contacts the first conductor in region 1506; regions 1514 and 1516 can be electrically contacted at an end of fiber 1500. However, the insulator in region 1508 includes recesses 1518 formed in the insulator such that region 1516 extends to an outer surface of fiber 1500 through recesses 1518. Also present but not visible in FIG. 15A are corresponding recesses in the insulator in region 1508 that allow region 1514 to extend to the outer surface of fiber 1500 on the other side of the fiber.

Figure 15B:
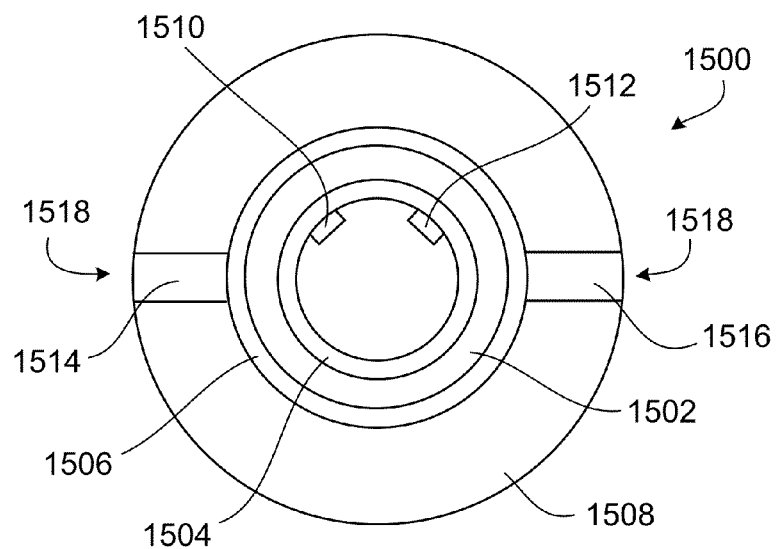
FIG. 15B is a cross-sectional view of the fiber of FIG. 15A.

FIG. 15B shows a cross-sectional view of the fiber shown in FIG. 15A through section line A-A. By virtue of recesses 1518, an external device such as electronic control circuit 1518 can directly contact regions 1514 and/or 1516 at locations along the length of fiber 1500 in addition to, or as an alternative to, contacting these regions at the end(s) of fiber 1500. Recesses 1518 thereby permit more flexible connections to internal elements of fiber 1500 for purposes of constructing functional devices. In some embodiments, lateral connections to internal fiber elements may be more structurally sound than connections formed at the ends of such fibers. Moreover, lateral connections may enable a greater number of circuits, processors, and other devices to be connected to such fibers.

Although recesses 1518 permit external connections only to regions 1514 and 1516 in fiber 1500, more generally recesses and other such structural features (e.g., grooves, channels, depressions, openings) can be used to permit access and connections to other internal elements within the fibers disclosed herein, including any of the regions of the first or second conductors present in the fibers. Further, although two rectangular recesses are shown in FIG. 15A on each side of fiber 1500, more generally a fiber can include any number and/or pattern of recesses formed in the insulator of region 1508. The recesses can have any shape convenient for purposes of facilitating contact between external devices and the exposed fiber elements, including rectangular, square, circular, elliptical, and other regular or irregular shapes.

In some embodiments, a spacer material can be positioned between the non-centrosymmetric material in the active region of a fiber and the first conductor in one or more of the regions that are adjacent to the active region. Spacer materials can be used, for example, to improve adhesion between conductors and non-centrosymmetric materials, while still maintaining good electrical contact between the materials. Exemplary spacer materials that can be used in the fibers disclosed herein include any one or more of the thermoplastic materials disclosed herein.

Applications

A wide variety of applications are enabled by the fibers disclosed herein. The fibers enable detection and emission (transduction) of acoustic waveforms at frequencies that range from tens of Hz to tens of MHz. Thus, for example, the fibers can be used as pressure sensors operating at frequencies of a few hundred Hz. At higher frequencies, arrays of fibers can be used as detection elements (e.g., in ultrasound imaging systems operating at tens of MHz). Due to the flexible and reproducible nature of the fiber drawing process, preforms can be readily constructed that incorporate desired functional elements of the fibers, and then the preforms can be drawn to yield the fibers. As such, specialized fibers can be readily engineered for specific applications.

In some embodiments, the fibers disclosed herein can be integrated with other functional elements. For example, as the conducting materials in the fibers disclosed herein correspond to electrical transmission elements, any of the conducting materials can be electrically connected to electronic elements such as power sources, transistors, amplifiers, and electrical gates.

In certain embodiments, some of the materials in the fibers can be used to guide optical waveforms. For example, the insulating material can be configured to guide optical waveforms introduced into the fiber, either in a central portion of the fiber (e.g., in a hollow portion of the fiber enclosed by region 104 in FIG. 1A), or in an outer portion of the fiber (e.g., in a portion of the insulator in region 108 in FIG. 1A). Further, in some embodiments, the fibers can include additional regions that include materials having different optical properties. For example, the fibers disclosed herein can include one or more additional regions formed of a material configured to guide optical waveforms along a length of the fiber. The one or more additional regions can extend along the fiber (e.g., along the common length of the fiber) to form optical transmission elements. As discussed previously, each of the additional regions can be formed of one or more materials with a viscosity of less than $10^7$ Poise and which maintain structural integrity and chemical composition at the common fiber draw temperature, to ensure that performs can be reproducibly drawn into high quality fibers.

In certain embodiments, one or more optoelectronic components or devices can be adjacent to and/or contacted with fiber elements including one or more of the conductors and/or the insulator. Exemplary optoelectronic components can include photodetectors, light sources such as lasers, and modulators such as acousto-optic modulators.

In some embodiments, the fibers disclosed herein can also include other functional components integrated into the fiber structure. For example, the fibers can include integrated optical components such as reflectors, Fabry-Perot cavities, photonic bandgap devices, and filters. A variety of different on-fiber applications can be enabled by such integration, including acousto-optic modulation.

To implement such integrated optical devices, the fibers can include one or more additional regions formed of materials with different optical properties, the additional regions extending along the length of the fibers (e.g., the common length of the fibers). The materials present in the additional regions are selected such that at the common fiber draw temperature, they have a viscosity of less than $10^7$ Poise, and maintain structural integrity and chemical composition.

Further, in certain embodiments, the fibers disclosed herein can include additional regions that include materials with different electrical properties. The additional regions extend along the length of the fibers (e.g., along the common length of the fibers). As above, the materials have a viscosity of less than $10^7$ Poise, and maintain structural integrity and chemical composition at the common fiber draw temperature. The materials in the additional regions can be positioned to implement a variety of different electronic devices within the fibers. For example, one or more of the additional regions can function as an electrical transmission line within the fiber. In some embodiments, the additional regions can implement more complex electronic devices such as signal detectors, transistors, amplifiers, resistors, gates, junctions, and/or logic devices.

Arrays of the acoustic fibers disclosed herein can be used for applications such as acoustic imaging; the fiber arrays can cover areas too large for conventional chip-based piezoelectric devices to successfully image. The fiber arrays can be assembled into flexible fabrics that permit real-time or near real-time imaging for applications such as emergency-care medicine and non-destructive mechanical testing of materials. For example, once woven into fabrics, the fibers are capable of acting as a communications transceiver. With small cross-sectional dimensions (e.g., on the order of tens to hundreds of microns) and long lengths (tens of meters or more), the fibers can be used to perform accurate pressure and/or flow measurements in small blood vessels (e.g., intercranial vessels), and in vivo endovascular imaging and microscopy within acoustically-opaque organs, for example.

In certain embodiments, the fibers disclosed herein can be used for a variety of remote sensing applications. The sensitivity of the fibers to mechanical perturbations such as stress and strain, and their low profile, make the fibers ideal functional elements that can be used to construct sparse sensor meshes for investigating large-area distributions of pressure and velocity fields in a variety of fluid flow applications (e.g., oceanic current monitoring).

In some embodiments, the fibers disclosed herein can be used for controlled release and/or delivery of substances. For example, as shown in the cross-sectional view of FIG. 16, a fiber 1600 can include a reservoir structure 1610 positioned at an end of the fiber. A valve 1612 traps molecules 1605 of a substance within reservoir structure 1610. Fiber 1600 also includes a non-centrosymmetric material in region 1602, a first conductor in regions 1604 and 1606, and an insulator in region 1608. Walls of reservoir 1610 are formed by the insulator in region 1608, the first conductor in regions 1604 and 1606, and the non-centrosymmetric material in region 1602. In some embodiments, only some of the materials of fiber 1600 may be used to form the walls of reservoir 1610. For example, reservoir 1610 may be positioned entirely within region 1602, or entirely within region 1608.

The plurality of molecules 1605 within reservoir 1610 can be controllably released. For example, the molecules can correspond to scents (e.g., perfumes) intended for release into the environment surrounding fiber 1600. Alternatively, the molecules can correspond to active chemical agents such as drugs that are intended for release when fiber 1600 is positioned at a particular site within a patient's body.

When release of the molecules contained within reservoir 1610 is desired, an acoustic wave is generated in fiber 1600, e.g., by applying a time-varying electric field between regions 1604 and 1606 in portion 1614 of fiber 1600. A propagating acoustic waveform 1616 is generated by the non-centrosymmetric material in region 1602 as a result. Acoustic waveform 1616 propagates along region 1602 until it reaches reservoir 1610. The presence of acoustic waveform in the portion of region 1602 that forms a wall of reservoir 1610 alternately enlarges and reduces an opening in valve 1612, permitting some of the molecules trapped within reservoir 1610 to leave the reservoir through the valve. Further, a portion of the acoustic energy of acoustic waveform 1616 is transferred to the trapped molecules 1605, increasing their kinetic energy and their diffusion rate through the opening in valve 1612.

As a result, trapped molecules can be controllably released from reservoir 1610 at desired locations and times. Moreover, because fiber 1600 efficiently propagates acoustic waveform 1616, the delivery end of fiber 1600 (e.g., the end in which reservoir 1610 is positioned) can be inserted into a patient, while the opposite end of the fiber (e.g., where acoustic waveform 1616 is introduced) remains outside of the patient.

In general, valve 1612 can be formed of any material that permits molecules 1605 to pass through when acoustic waveform 1616 creates a mechanical disturbance in the valve. In some embodiments, for example, valve 1612 can be formed of a material with a permeability that can be varied by introducing an acoustic waveform into the material.

Molecules 1605 can also have one or more properties that can assist in their selective release at a target site. For example, in some embodiments, molecules 1605 include particles with a particle size that can change when excited by an acoustic waveform. By coupling an acoustic waveform into reservoir 1610, the sizes of the particles can be reduced, facilitating exit from reservoir 1610 through valve 1612.

In certain embodiments, molecules 1605 have a viscosity and/or a diffusivity that can change when excited by an acoustic waveform. By coupling an acoustic waveform into reservoir 1610, the viscosity of molecules 1605 can be reduced and/or the diffusivity of molecules 1605 can be increased, facilitating exit of the molecules from reservoir 1610.

Figure 16:
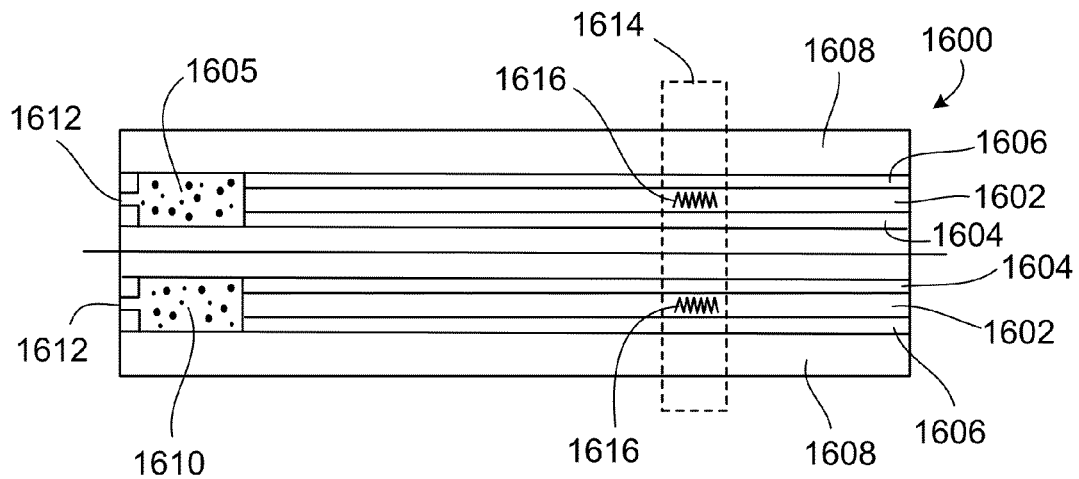
FIG. 16 is a sectional view of a fiber with a reservoir.

In FIG. 16, valve 1612 is positioned so that molecules 1605—when leaving reservoir 1612—enter a region outside fiber 1600. In some embodiments, valve 1612 can be positioned so that molecules 1605, when the leave reservoir 1610 through valve 1612, enter a hollow portion of fiber 1600, e.g., the hollow central region of fiber 1600. Reservoir 1610 can also include more than one valve; certain valves can lead to regions external to fiber 1600, while others can lead to internal regions of fiber 1600.

Further, in FIG. 16, reservoir 1610 is formed within one or more of regions 1602, 1604, 1606, and 1608. In certain embodiments, however, the hollow central region of fiber 1600 can function as a reservoir in addition to, or as an alternative to, a reservoir positioned as in FIG. 16. Molecules 1605 can be trapped within the hollow region of fiber 1600 by a valve 1612. Acoustic excitation of the valve and/or the trapped molecules can lead to dispersal of some of the molecules into a region outside fiber 1600.

Although FIG. 16 shows a fiber 1600 with a single reservoir 1610 with trapped molecules or particles, more generally the fibers disclosed herein can include multiple reservoirs, each with an associated region of non-centrosymmetric material. In some embodiments, for example, fibers can include two or more regions of non-centrosymmetric material, each having one or more associated reservoirs, and the one or more reservoirs associated with each region of non-centrosymmetric material can include different types of trapped molecules. By inserting such fibers into patients, for example, controlled release of different types of therapeutic agents at specific locations and times can be achieved.

EXAMPLES

The following examples are not intended to limit the scope of the disclosure or the claims. Acoustic fibers were prepared according to the methods discussed above. Both cylindrical fibers (e.g., as shown in FIG. 1A) and planar fibers (e.g., as shown in FIGS. 12A and 12B) were fabricated using P(VDF-TrFE) as the non-centrosymmetric material, conductive polycarbonate (e.g., polycarbonate doped with carbon) to form the first conducting material, indium filaments to form the second conducting material, and undoped polycarbonate as the insulating material. At the fiber draw temperature, the conductive polycarbonate material had a viscosity of $10^5$-$10^6$ Poise. Upon cooling, the conductive polycarbonate material had a resistivity of about $1\sim10^4$ Ω·m within a frequency range from 0 Hz to several tens of MHz. As a result, the conductive polycarbonate material facilitated short-range (e.g., hundreds of microns) charge transport on length scales that were approximately equivalent to the fiber cross-sectional dimensions.

Figure 17A:
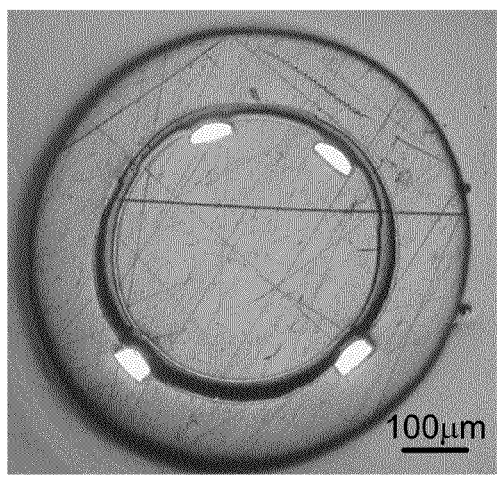
FIG. 17A is a scanning electron microscope image of a cross-sectional surface of a cylindrical fiber.
Figure 17B:
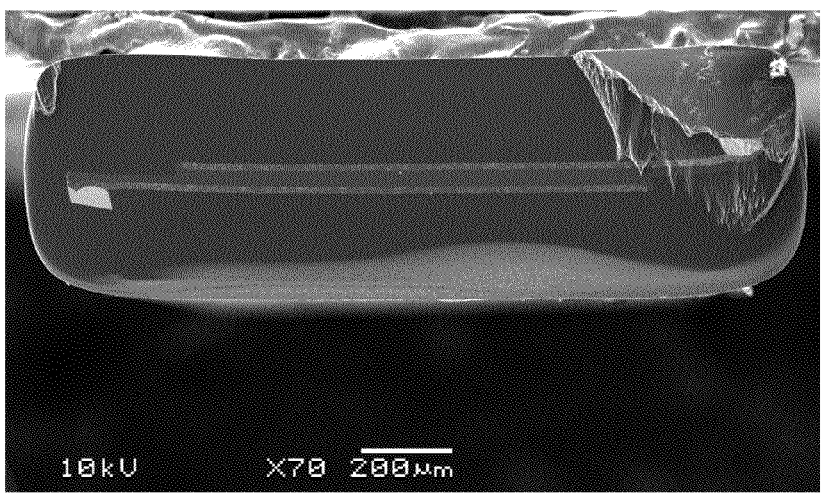
FIG. 17B is a scanning electron microscope image of a cross-sectional surface of a fiber that includes a planar material stack.
Figure 17C:
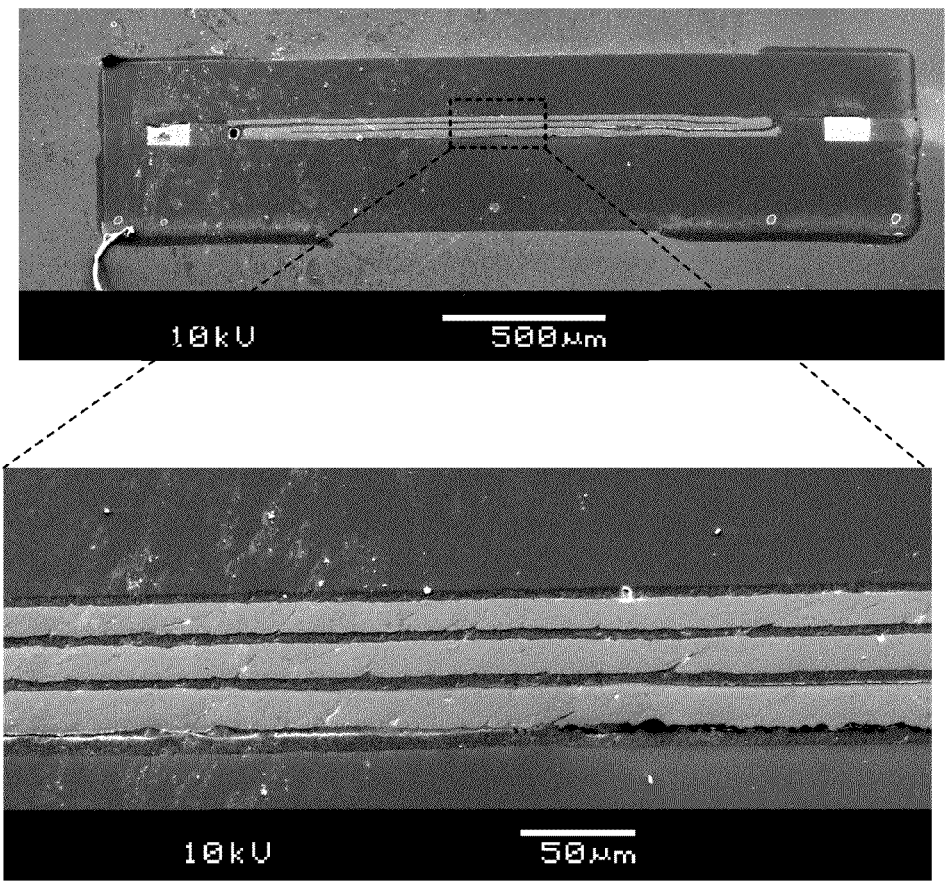
FIG. 17C is a scanning electron microscope image of a cross-sectional surface of a fiber with a folded internal geometry.

The indium filaments and conductive polycarbonate (CPC) form electrodes extending along the full length of the fiber. Specifically, the CPC portion of each electrode provides large surface area contact with the P(VDF-TrFE), while the indium filaments function as a longitudinal "bus" that increases the conductivity of each electrode over the full length of the fiber. Scanning electron microscope images of exemplary fabricated fibers are shown in FIGS. 17A and 17B. In addition, fibers with folded internal geometries that included multiple layers of P(VDF-TrFE) were also fabricated; a scanning electron microscope image of an exemplary fiber is shown in FIG. 17C.

Embedding piezoelectric domains that can be poled in a fiber's cross section allows fibers to be electrically actuated over broad frequencies on the one hand, and to function as sensitive broadband microphones on the other. To-date, however, fibers for the most part have been made of materials in the disordered glassy state precluding the symmetry requirements for piezoelectricity. Moreover, the need to apply electric fields to the piezoelectric material implies inclusion of conducting electrodes within the fiber cross-section, which presents a number of significant processing challenges.

Using the methods disclosed herein, fiber materials are drawn from preforms in a regime dominated by viscous forces allowing for internal low viscosity domains to be arranged in non-equilibrium cross sections confined by viscous glassy boundary layers. Preforms can include a material such as poly(vinylidene fluoride) (PVDF), metal electrodes, and an insulating polymer. Thermally drawing such preforms would lead to fibers with a non-centrosymmetric material therein (the stress present during the fiber draw induces the non-polar a to the ferroelectric (3 phase transition in the PVDF layer). However, a variety of different material processing challenges are manifest at different length scales in such fibers. On the hundreds of microns length scale, the use of crystalline materials both for the piezoelectric layer and the electrical conductors leads to the formation of multiple adjacent low viscosity domains of high aspect ratio. These domains can undergo a significant reduction in cross sectional dimensions during the fiber draw, and are therefore susceptible to capillary breakup and mixing due to flow instabilities. At the tens of microns length scale, layer thickness variations either in the lateral or in the longitudinal directions can impede the formation of coercive fields needed for poling. Further, on molecular length scales, even if capillary breakup was kinetically averted and uniform sections of fibers at meter lengths were drawn, such fibers might not exhibit piezoelectricity if the stress and strain conditions necessary to induce the thermodynamic phase transition in PVDF are not sustained during the fiber draw process.

To address the various fiber material processing challenges, fibers were constructed using viscous and conductive carbon-loaded poly(carbonate) (CPC) layers that were used to confine the low viscosity crystalline piezoelectric layer during the draw process. The CPC layers exhibited high viscosity ($10^5\sim10^6$ Pa·s) at the draw temperature, and adequate resistivity ($1\sim10^4$ Ω·m) over the frequency range from DC to tens of MHz, thus facilitating short range (hundreds of microns) charge transport on length scales associated with the fiber cross section. Further, a piezoelectric polymer, poly (vinylidene fluoride-trifluoroethylene) copolymer (P(VDF-TrFE)), which assumes the ferroelectric β phase spontaneously upon solidification from the melt without application of mechanical stress, was used as the non-centrosymmetric material in the drawn fibers.

Figure 20:
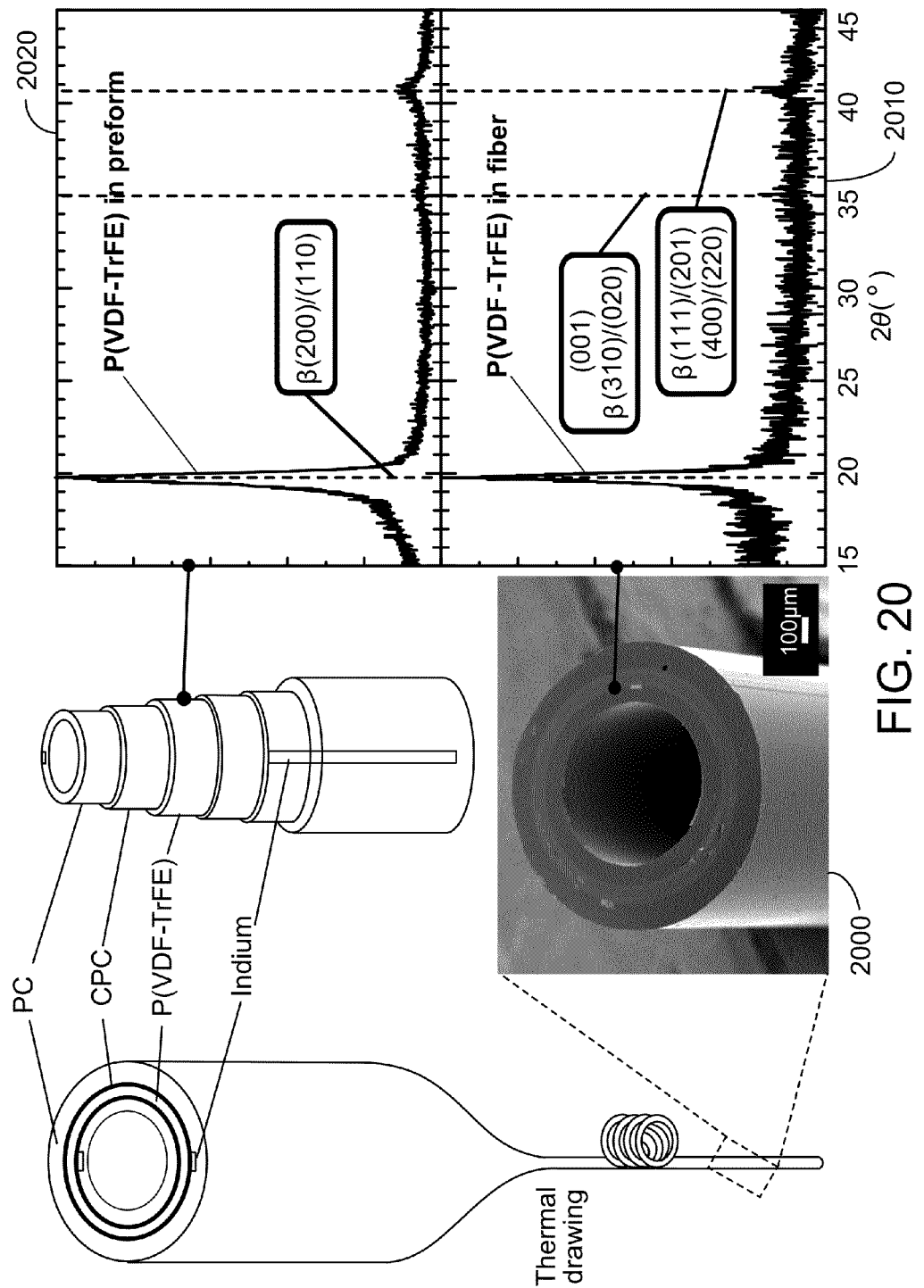
FIG. 20 is a schematic diagram of a cylindrical fiber preform.

The constituent fiber materials were assembled as illustrated in FIG. 20. A series of shells, including a 700 μm-thick layer of P(VDF-TrFE) (70:30 molar ratio, melt-pressed from pellets obtained from Solvay, Brussels, Belgium) and multiple 250 μm-thick layers of CPC were assembled with indium filaments and a poly(carbonate) (PC) cladding. The entire structure was consolidated at 210° C. to remove trapped gas and form high quality interfaces. The preform was then thermally drawn in a furnace at 230° C. into fibers more than 100 meters long. Drawing occurred in a three-zone vertical tube furnace at a down-feed speed of 1 mm/minute. Drawn fiber dimensions were monitored with laser micrometers.

The stability of the draw was monitored by a continuous in-line measurement of the external dimensions of the fiber by a laser micrometer. The standard deviation was calculated over a 10 cm window in real-time and maintained at a level below 1% by controlling the draw stress. Since uniformity of the external geometry of the fiber does not ensure that of the internal structure, Scanning Electron Microscopy (SEM) was used to image cross-sections of the fiber and to evaluate the uniformity of the piezoelectric polymer layer thickness across its width. Among the drawn fibers, a standard deviation in the polymer layer thickness of 3% was measured.

To investigate the uniformity of structure along the length of the fiber, a one meter-long portion of the fiber was cut into 3 cm-long segments, and the capacitance of each segment was measured. Fluctuation in the average thickness of the piezoelectric P(VDF-TrFE) layer should result in a proportional fluctuation on the capacitance, and a standard capacitance deviation among the sections of 4% was measured.

A scanning electron microscopy (SEM) image 2000 of the fiber cross section in FIG. 20 shows the P(VDF-TrFE) layer (determined to be 40 μm thick from the image) sandwiched between CPC layers, with the shape and the aspect ratio unchanged from those of the preform. FIG. 20 also shows a wide angle X-ray diffraction (XRD) scan 2010 of a P(VDF-TrFE) copolymer domain harvested from the drawn fiber, and a XRD scan 2020 of the preform. Both the drawn fiber and the preform exhibit identical diffraction peaks at 2θ=19.9, 35.2, and 40.7 degrees, which correspond to (200)/(110), (001) and (310)/(020), (111)/(201) and (400)/(220) peaks of the β-phase of P(VDF-TrFE), establishing that the drawn copolymer in each fiber solidified in its β-phase. The crystallinity fraction as calculated from XRD patterns was over 90%. The obtained fiber was then poled by applying through the internal fiber electrodes an electric field in excess of 60 MV/m, a field strength greater than the reported coercive field strength for P(VDF-TrFE). Long lengths of fiber were readily poled in this way.

To characterize the acoustic properties of the fabricated fibers, motion of the fiber surface in response to internal piezoelectric modulation was first measured using a heterodyne optical vibrometer at kHz frequencies (e.g., where fiber dimension is much smaller than the acoustic wavelength). The vibrometry apparatus included a frequency-swept (1530-1570 nm, at 80 nm/s) laser (Agilent Technologies, 8164B) coupled to a fiber-optic Michelson interferometer and a Fabry-Perot frequency reference. The two arms of the Michelson interferometer differed in length and generated a heterodyne beat tone. In one arm, light was focused onto the vibrating surface of the fiber, where the Doppler shift of the reflected light produced additional frequency-modulation sidebands on the beat tone. The Fabry-Perot reference provided real-time frequency calibration. With this information, the frequency chirp in the swept-laser source was compensated when processing the interferometry data.

Figure 21:
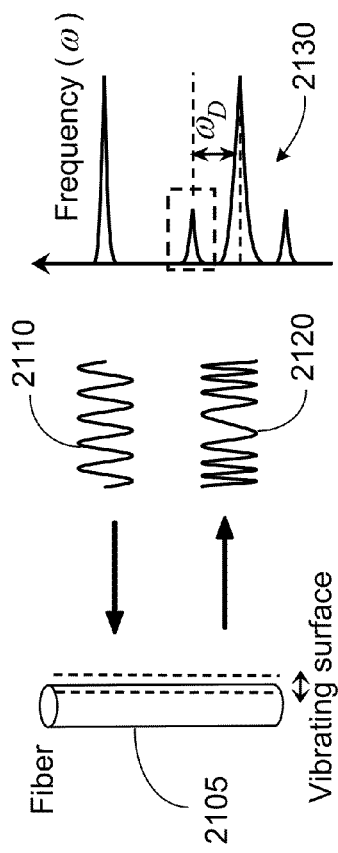
FIG. 21 is a schematic diagram of an optical vibrometer apparatus.
Figure 21:
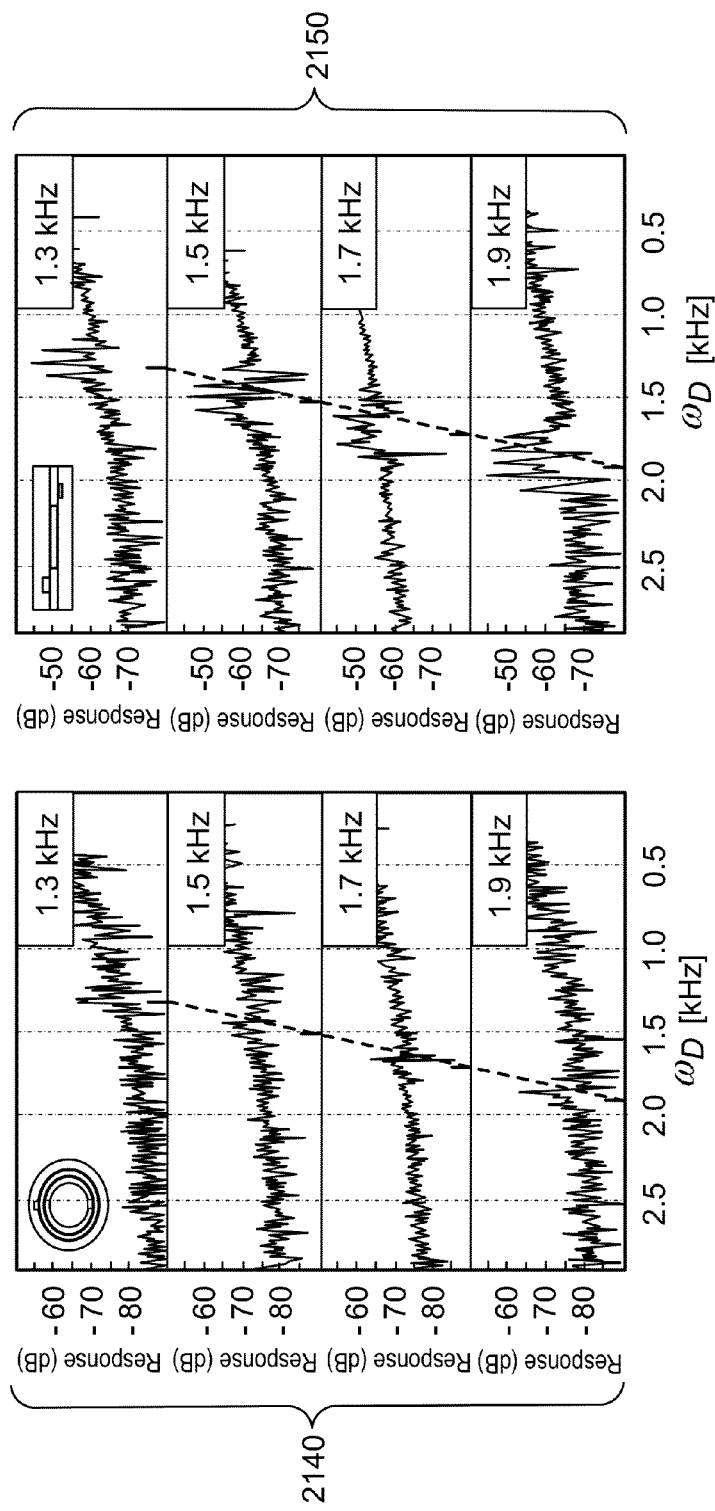

As shown schematically in FIG. 21, fibers (e.g., fiber 2105) were electrically driven by a sine wave with a maximum amplitude of 10 V. The vibrating fiber surface functioned as an oscillating reflector; the frequency of incident light 2110 was Doppler-shifted, and the frequency-shifted reflected light 2120 was measured by the optical vibrometer. A series of frequency-modulation (FM) side bands spaced at the modulation frequency ωD were observed in the spectrum 2130 of the reflected radiation. The amplitudes of the side bands were proportional to the velocity amplitude of the vibrations. Spectrum 2140 shows a series of side bands for the cylindrical fiber of FIG. 20 driven at several frequencies from 1.3 to 1.9 kHz. The measured side bands establish a macroscopic piezoelectric response from the embedded ferroelectric layers in the fibers. The side band amplitude modulation response was found at ~−60 dB below the main beat tone around these frequencies.

Spectrum 2150 shows similar frequency-modulation side bands for a rectangular fiber with an embedded planar piezoelectric layer, fabricated using a technique similar to the one described above (see below). The rectangular geometry coupled more efficiently to the optical beam leading to a marked improvement in the signal measured in the side bands compared to the immediate background. It also lead to a 20 dB increase in the side band amplitude with respect to the heterodyne sub-carrier.

Figure 18:
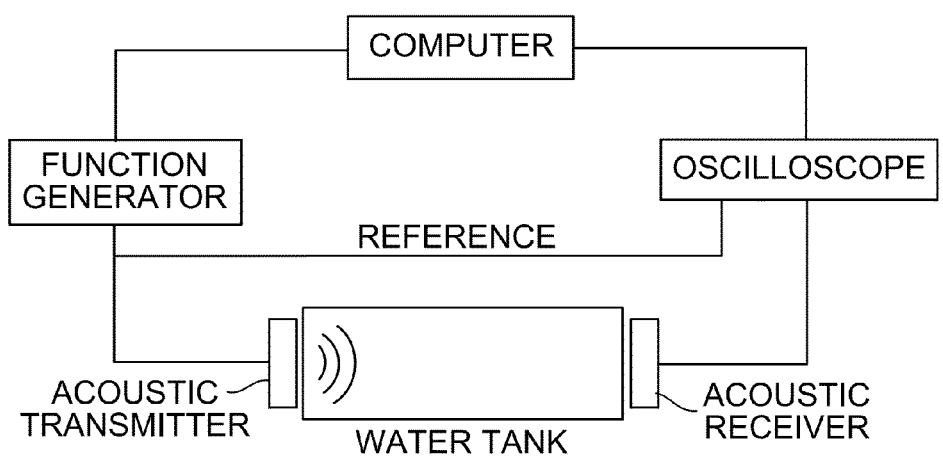
FIG. 18 is a schematic diagram of an acoustic transmission test apparatus.

Direct acoustic measurements were then performed on the drawn fibers, using the fibers as both an acoustic sensor and an acoustic actuator centered at 1 MHz. Such a frequency range is typical in ultrasound imaging applications. The apparatus used to perform the experiments is shown schematically in FIG. 18. As shown in FIG. 18, a computer was connected to both a function generator and an oscilloscope. When a fiber was evaluated as a detector, the fiber was connected to the oscilloscope (e.g., as the "Acoustic Detector") and a commercial piezoelectric transducer was connected to the function generator (e.g., as the "Acoustic Transmitter"). The transducer and the fiber were coupled across a water tank to match the acoustic impedance. The computer was configured to generate an arbitrary electrical waveform via the function generator. The commercial transducer, acting as the transmitter, received the electrical waveform and generated a corresponding acoustic waveform in the water tank. The fiber, acting as the detector, received the propagating acoustic signal and generated a corresponding electrical signal that was transmitted to the oscilloscope and the computer. The electrical waveform generated by the computer via the function generator was then compared to the waveform detected by the fiber.

In contrast, when the fiber was evaluated as a transmitter, the positions of the fiber and the commercial piezoelectric transducer were reversed (e.g., the fiber was connected to the function generator and the commercial transducer was connected to the oscilloscope) and the procedure was repeated to again compare the computer-generated waveform to the detected waveform.

Figure 22A:
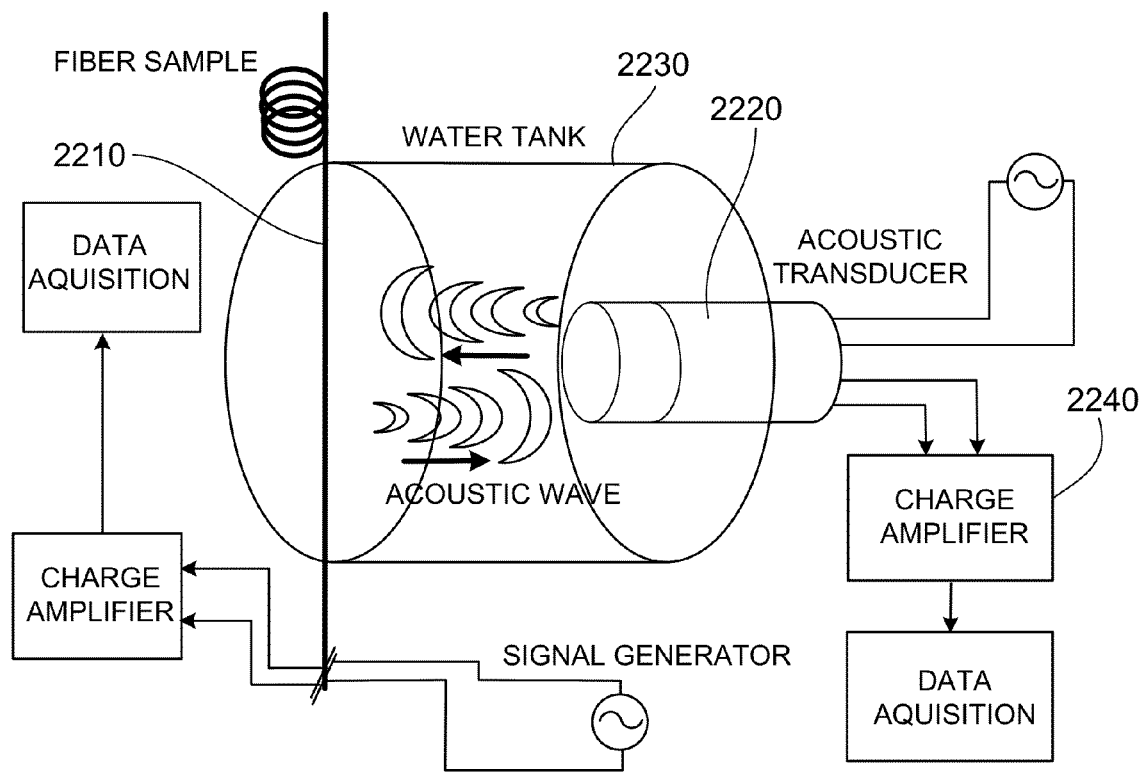
FIG. 22A is a schematic diagram of an apparatus used to measure acoustic responses of drawn fibers.

A more detailed schematic of the experimental apparatus is shown in FIG. 22A. A water-immersion ultrasonic transducer 2220 (Olympus Panametrics-NDT, 1.0 MHz-centered) was coupled to a 30 mm long fiber 2210 across a water tank 2230 to match the acoustic impedance. Fiber 2210 was attached to the surface of water tank 2230 via immersion gel, with the piezoelectric layer facing towards transducer 2220. The transducer-to-fiber distance was approximately 97 mm, roughly 70 acoustic wavelengths at 1 MHz. At MHz frequencies, capacitive electromagnetic coupling between the transducer circuit and the receiver charge amplifier 2240 can be significant even with careful shielding and grounding. To separate the acoustic signals from the electromagnetic interference, pulsed excitation of fiber 2210 was used, and the received signals were time-gated to exploit the 5 orders of magnitude difference in the propagation speed between acoustic and electromagnetic pulses. Temporal traces of the amplified voltages under a pulsed excitation were measured with a carrier frequency at 600 kHz and a 52 μs temporal envelope at a 6.5 kHz repetition rate. The time delays of the received pulses were consistent with acoustic propagation in water at 1470±30 m/s, as demonstrated by temporal scans 2250 in FIG. 22B showing measurements of the received pulses.

Figure 22C:
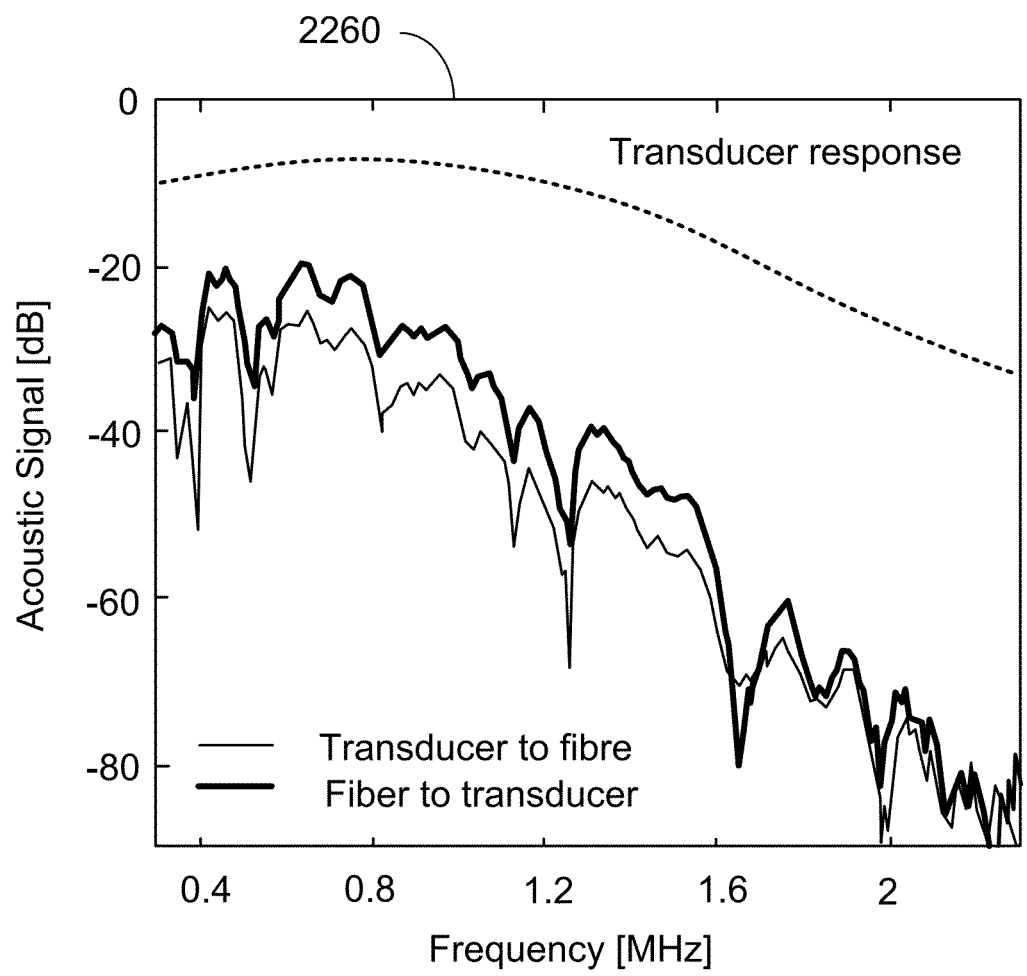
FIG. 22C is a plot of acoustic signal as a function of frequency for a flat rectangular piezoelectric fiber.

Frequency domain characterizations of flat rectangular piezoelectric fibers were performed with a fixed transducer-to-fiber distance, with pulsed fiber excitation, and with time-gated signal processing. A spectrum 2260 showing the frequency response of a typical flat fiber is shown in FIG. 22C. The measured piezoelectric response of the fiber, both as a sensor and an actuator, essentially followed the intrinsic frequency profile of the transducer. Although the frequency range was limited here by the bandwidth of the transducer, polymeric piezoelectric elements are in principle broadband and the piezoelectric fibers could have operated at a far broader range of frequencies. For example, similar fibers were used to generate audible sound between 7 kHz and 15 kHz with a driving voltage of 5V.

Figure 19A:
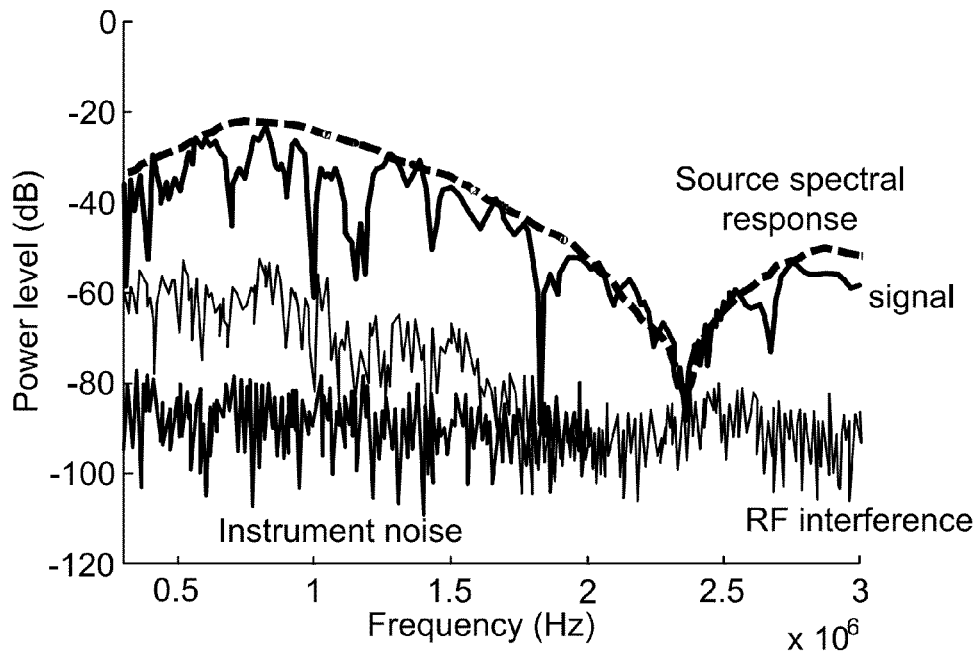
FIG. 19A is a plot showing a comparison between measured and reference acoustic signals for a fiber used as an acoustic detector.
Figure 19B:
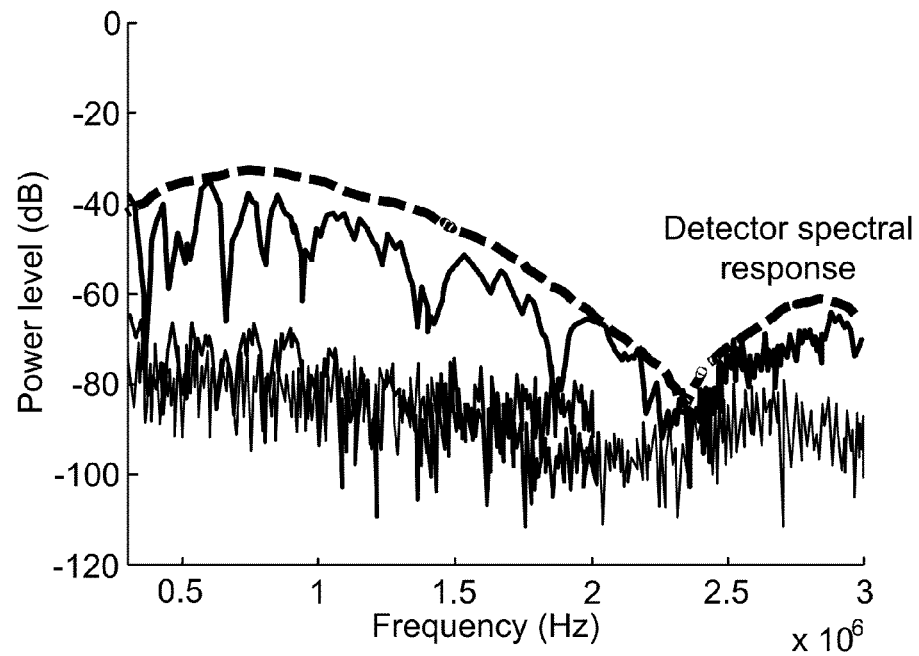
FIG. 19B is a plot showing a comparison between measured and reference acoustic signals for a fiber used as an acoustic transmitter.

FIG. 19A shows a comparison between the computer-generated waveform (dotted line) and the measured acoustic signal (solid line) when the fiber acts as a detector. The frequency response of the fiber as a detector generally matched the frequency spectrum of the source transducer (note that the ripples were due to acoustic resonances in the water tank). FIG. 19B shows a comparison between the computer-generated waveform (dotted line) and the measured acoustic signal (solid line) when the fiber acts as a transmitter. The frequency response of the fiber transmitter included spectral features that were similar to those of the commercial transducer. As in FIG. 19A, ripples in the measured acoustic response were due to resonances in the water tank.

Figure 23:
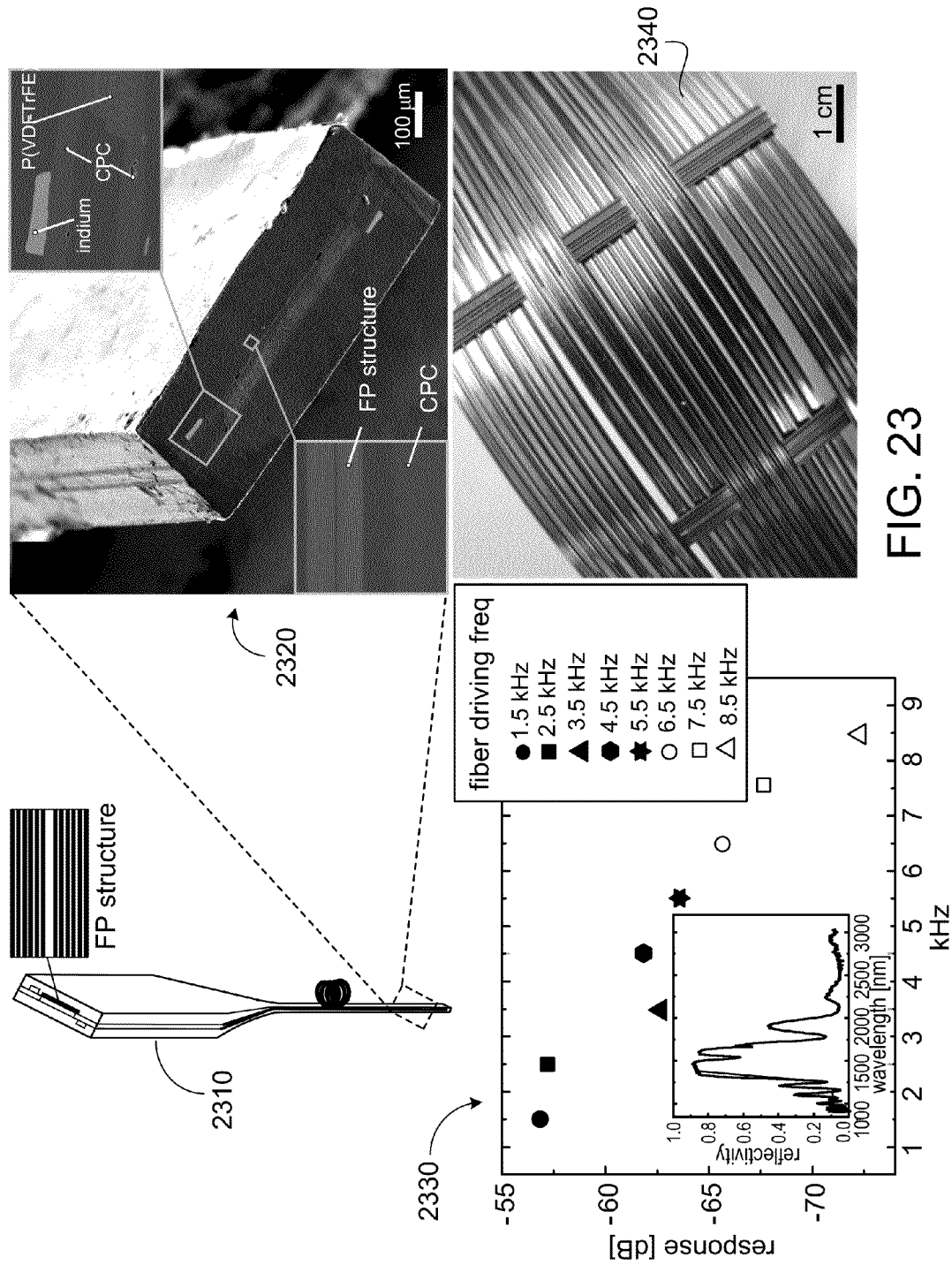
FIG. 23 is a schematic diagram of a rectangular fiber preform.

To further, demonstrate the flexibility of the methods disclosed herein, a rectangular fiber (as discussed briefly above) was fabricated with a Fabry-Perot (FP) optical cavity structure layered on an embedded piezoelectric element. FIG. 23 shows a schematic diagram of the fiber preform 2310 being drawn into a fiber. To fabricate the fiber, a macroscopic preform 32 mm in width and 11 mm in thickness was assembled. The preform was 25 cm long and included a 1.4 mm-thick layer of P(VDF-TrFE) contacted by CPC and indium electrodes, and sandwiched between protective PC plates. The preform was consolidated in a hot press at 175° C. and subsequently drawn in a three-zone vertical tube furnace with a top-zone temperature of 150° C., a middle-zone temperature of 230° C., and a down-feed speed of 1 mm/minute. The fiber dimensions were monitored with laser-micrometers. A capstan speed of 0.5-3 m/minute produced a fiber of width between about 2,000 and 600 μm and a length of several hundred meters.

A SEM image 2320 of an exemplary drawn rectangular fiber shows that the piezoelectric drawn fiber was 800 μm wide and exhibited well-maintained preform-to-fiber dimensional ratio and adhesion of the structures. Reflectivity of the piezoelectric FP fiber was characterized with a Fourier transform infrared (FTIR) microscope (Bruker Optics, Tensor/

Hyperion 1000), revealing that reflectivity reached 90% at a wavelength of about 1500 nm. The spectral dip associated with the FP resonant mode was identified at 1550 nm.

As described above, heterodyne interferometry was used to characterize the fiber vibration produced by the embedded piezoelectric material. The piezoelectric FP fiber was electrically driven by a sine wave at frequencies stepped from 1.5 through 8.5 kHz with a maximum driving wave amplitude of 10V. An optical probe beam was focused on the FP structure to take advantage of the enhanced reflection from the bulk structure. Spectrum 2330 shows the frequency dependence of the side band amplitude measured for the FP fiber; these results suggest signals enhanced or damped by underlying acoustic resonances of the fiber sample.

The piezoelectric FP fibers were mechanically robust yet flexible, and were capable of assembly into a fabric 2340 for large area coverage, as shown in FIG. 23. The color of the fabric resulted from reflection from the third order band of the Fabry-Perot optical structure embedded in the fibers.

Other Embodiments

A number of embodiments have been described. Nevertheless, it will be understood that various modifications may be made without departing from the spirit and scope of the disclosure. Accordingly, other embodiments are within the scope of the following claims.

What is claimed is:

1. A fiber comprising a composite of at least three different materials,
    said at least three different materials comprising a conductor, an insulator, and a material that is in a microscopic non-centrosymmetric crystalline phase,
    each material being disposed in one or more different cross-sectional regions of the fiber, with each region extending along a common length of the fiber,
    said conductor comprising a conductive material disposed in direct contact with the non-centrosymmetric crystalline phase material; and
    wherein at a common fiber draw temperature said conductive material has a viscosity that is higher than that of the material in a non-centrosymmetric crystalline phase.

2. The fiber of claim 1, wherein at a common fiber draw temperature, each of said at least three different materials has a viscosity that is less than about $10^7$ Poise.

3. The fiber of claim 2, wherein at the common fiber draw temperature, each of said at least three different materials maintains structural integrity.

4. The fiber of claim 2, wherein at the common fiber draw temperature, each of said at least three different materials maintains chemical composition.

5. The fiber of claim 1, wherein the material that is in a non-centrosymmetric crystalline phase comprises a piezoelectric material.

6. The fiber of claim 5, wherein the piezoelectric material comprises a ferroelectric material.

7. The fiber of claim 1, wherein the conductive material is a first conductor, and further comprising a second conductor, the second conductor being disposed in contact with the first conductor in one or more additional cross-sectional regions of the fiber that extend along the common length of the fiber.

8. The fiber of claim 7, wherein the first conductor has a viscosity that is greater than about $10^2$ Poise at the common fiber draw temperature and the second conductor has a conductivity greater than that of the first conductor.

9. The fiber of claim 7, wherein the second conductor electrically contacts the first conductor along the common length of the fiber.

10. The fiber of claim 7, wherein:
    a first set of the cross-sectional regions comprising the first and second conductors in electrical contact with one another define a first electrode;
    a second set of the cross-sectional regions comprising the first and second conductors in electrical contact with one another define a second electrode;
    one of the cross-sectional regions comprising the material that is in a non-centrosymmetric crystalline phase defines an active region; and
    the first and second electrodes are positioned on opposite sides of the active region.

11. The fiber of claim 10, wherein the first conductor has a viscosity that is greater than about $10^2$ Poise at the common fiber draw temperature and the second conductor has a conductivity greater than that of the first conductor.

12. The fiber of claim 10, wherein the first conductor in each of the electrodes contacts the material that is in a non-centrosymmetric crystalline phase in the active region and has a viscosity greater than that of the second conductor.

13. The fiber of claim 10, further comprising a spacer material positioned between the material that is in a non-centrosymmetric crystalline phase in the active region and the first conductor in each of the electrodes.

14. The fiber of claim 10, wherein the material that is in a non-centrosymmetric crystalline phase can sustain a field of 3 MV/m or more when an electrical potential difference is applied between the first and second electrodes.

15. The fiber of claim 10, wherein the material that is in a non-centrosymmetric crystalline phase in the active region causes an acoustic waveform to be emitted from the fiber when an electrical potential difference is applied between the first and second electrodes.

16. The fiber of claim 15, wherein a frequency of the acoustic waveform corresponds to a frequency of the electrical potential difference.

17. The fiber of claim 10, wherein the material that is in a non-centrosymmetric crystalline phase in the active region generates an electrical potential difference corresponding to an electrical waveform between the first and second electrodes when an acoustic waveform impinges on the non-centrosymmetric material.

18. The fiber of claim 17, wherein a frequency of the electrical waveform corresponds to a frequency of the acoustic waveform.

19. The fiber of claim 7, wherein the second conductor comprises one or more metals.

20. The fiber of claim 19, wherein the second conductor comprises an alloy of two or more metals.

21. The fiber of claim 19, wherein the one or more metals comprise at least one of bismuth, lead, tin, indium, cadmium, gallium, copper, aluminum, silver, gold, and zinc.

22. The fiber of claim 1, wherein a cross-sectional shape of the conductor has a maximum length measured along an outer surface of the conductor and a thickness measured in a direction orthogonal to the outer surface, and wherein a ratio of the maximum length to the thickness is 3 or more.

23. The fiber of claim 1, wherein the fiber has an outer perimeter that is one of circular, elliptical, rectangular, square, triangular, and polygonal in shape.

24. The fiber of claim 1, wherein the fiber has a length of 10 centimeters or more, and a maximum cross-sectional dimension of 2 mm or less.

25. The fiber of claim 10, wherein the first conductor in each of the electrodes extends to an outer surface of the fiber along at least a portion of the common length of the fiber.

26. The fiber of claim 1, wherein the fiber is drawn from a preform having a length that is smaller than a length of the fiber.

27. The fiber of claim 1, wherein the at least three different materials are disposed in an all-solid fiber cross section.

28. The fiber of claim 1, further comprising:
one or more additional regions positioned within the cross-section of the fiber and comprising materials with different optical properties, the one or more additional regions forming an optical transmission element extending along at least a portion of the common length of the fiber,
wherein, at the common fiber draw temperature, each of the materials within the one or more additional regions has a viscosity that is less than about $10^7$ Poise and maintains structural integrity and chemical composition.

29. The fiber of claim 1, further comprising:
one or more additional regions positioned within the cross-section of the fiber and comprising materials with different optical properties, the one or more additional regions forming an optical device extending along at least a portion of the common length of the fiber,
wherein, at the common fiber draw temperature, each of the materials within the one or more additional regions has a viscosity that is less than about $10^7$ Poise and maintains structural integrity and chemical composition.

30. The fiber of claim 1, further comprising:
one or more additional regions positioned within the cross-section of the fiber and comprising materials with different electrical properties, the one or more additional regions forming an electronic device extending along at least a portion of the common length of the fiber,
wherein, at the common fiber draw temperature, each of the materials within the one or more additional regions has a viscosity that is less than about $10^7$ Poise and maintains structural integrity and chemical composition.

31. The fiber of claim 1, wherein the insulator comprises a polymeric insulating material or a high temperature insulating material comprising at least one of silica and silicate glass.

32. The fiber of claim 31, wherein the polymeric insulating material comprises a material having a high glass transition temperature.

33. The fiber of claim 31, wherein the polymeric insulating material comprises at least one of a polyimide material, a polysulfone material, a polycarbonate material, a polymethacrylate material, a polyester material, a polyacrylate material, a polyether sulfone material, a cyclic olefin material, and a fluorinated polymer material.

34. The fiber of claim 31, wherein the polymeric insulating material comprises a thermoplastic material.

35. The fiber of claim 1, wherein:
the conductive material comprises a composite of a host material and conducting particulates;
the host material comprises at least one material selected from the group consisting of a polycarbonate material, a polyethylene material, an acrylonitrile-butadiene-styrene copolymer material, an acetal copolymer material, a polypropylene material, a polyvinylidene fluoride material, and a polyetherimide material; and
the conducting particulates comprise at least one material selected from the group consisting of carbon particles, carbon fibers, carbon nanotubes, and stainless steel fibers.

36. The fiber of claim 1, wherein the material that is in a non-centrosymmetric crystalline phase comprises at least one of a poly(vinylidene fluoride) material, a copolymer material of vinylidene fluoride and trifluoroethylene, a polyvinyl chloride material, a copolymer material of vinyl acetate and vinylidene cyanide, a nylon polymer material, a nylon copolymer material, a polyacrylonitrile material, and a high temperature ceramic material comprising at least one of lead zirconate titanate, quartz, barium titanate, and cadmium sulfide.

37. The fiber of claim 1, wherein an electrical resistivity of the conductor is $10^5$ ohm·m or less.

38. The fiber of claim 1, wherein an electrical resistivity of the insulator is $10^8$ ohm·m or more.

39. The fiber of claim 1, wherein a dielectric strength of the insulator is 10 MV/m or more.

40. The fiber of claim 1, further comprising a reservoir positioned within the fiber.

41. The fiber of claim 40, wherein the material that is in a non-centrosymmetric crystalline phase forms at least one wall of the reservoir.

42. The fiber of claim 40, wherein:
the material that is in a non-centrosymmetric crystalline phase causes an acoustic waveform to be emitted from the fiber when an electrical potential difference is applied between the first and second electrodes; and
wherein the acoustic waveform is configured to cause a substance present within the reservoir to leave the reservoir through a valve positioned in a wall of the reservoir.

43. The fiber of claim 42, wherein the valve is positioned so that the substance leaving the reservoir emerges from an end of the fiber.

44. The fiber of claim 42, wherein the valve is positioned so that the substance leaving the reservoir emerges into a hollow region of the fiber.

45. The fiber of claim 42, wherein the valve comprises a material having a permeability for the substance that can be varied by introducing an acoustic waveform into the material.

46. The fiber of claim 42, wherein the substance comprises at least one of:
a plurality of particles having a particle size that can be varied by introducing an acoustic waveform into the substance;
a viscosity that can be varied by introducing an acoustic waveform into the substance; and
a diffusivity that can be varied by introducing an acoustic waveform into the substance.

47. A drug delivery system, the system comprising:
the fiber of claim 40; and
an electrical source coupled to the fiber to selectively cause delivery of a drug material in the reservoir.

48. The fiber of claim 40, wherein the reservoir is positioned at least partially within a region comprising the insulator or at least partially within a region comprising the first conductor.

49. An acoustic wave detector, the detector comprising:
the fiber of claim 1; and
an electrical detector coupled to the fiber to detect an electrical signal produced by the non-centrosymmetric material in response to the acoustic wave.

50. The detector of claim 49, further comprising a plurality of fibers corresponding to the fiber of claim 1, wherein the plurality of fibers are configured to form a fiber array.

51. An acoustic wave generator, the generator comprising:
the fiber of claim 1; and
an electrical source coupled to the fiber to selectively cause the non-centrosymmetric material in the fiber to generate the acoustic wave.

52. A method for producing a fiber comprising a composite of at least three different materials, the method comprising:
assembling a fiber preform comprising the at least three different materials, wherein the at least three different materials include a conductor, an insulator, and a material that is in a having microscopic non-centrosymmetric crystalline phase, with said conductor comprising a conductive material disposed in contact with the non-centrosymmetric crystalline phase material; and
drawing the preform into a fiber at a fiber draw temperature at which said conductive material has a viscosity that is higher than that of the non-centrosymmetric crystalline phase material, the fiber comprising each of the at least three different materials disposed in one or more different cross-sectional regions of the fiber.

53. The method of claim 52, wherein at the fiber draw temperature, each of the at least three different materials has a viscosity that is less than about $10^7$ Poise.

54. The method of claim 52, wherein each of the at least three different materials maintains structural integrity and chemical composition when the preform is drawn into the fiber.

55. The method of claim 52, further comprising maintaining a drawing tension of 5 grams or more per square millimeter of the preform cross-sectional area as the preform is drawn to form the fiber.

56. The method of claim 53, further comprising cooling the fiber after the preform is drawn, wherein the material that is in a non-centrosymmetric crystalline phase solidifies in the non-centrosymmetric crystalline phase when the fiber is cooled.

57. The method of claim 56, wherein applying the electrical potential difference comprises applying a direct current potential difference of 10 V or more per micrometer of thickness of the material that is in a non-centrosymmetric crystalline phase.

58. The method of claim 52, further comprising annealing the fiber for a period of one hour or more at a temperature of between 120° and 150° C.

59. The method of claim 52, wherein:
a cross-sectional region that comprises the material that is in a non-centrosymmetric crystalline phase defines an active region;
the conductor is disposed in a first set of cross-sectional regions that define a first electrode, and in a second set of cross-sectional regions that define a second electrode, the first and second electrodes being positioned on opposite sides of the active region; and
the method further comprising applying an electrical potential difference between the first and second electrodes to align domains within the material that is in a non-centrosymmetric crystalline phase.

60. The method of claim 59, wherein the conductor is a first conductor, and wherein the at least three different materials further comprise a second conductor disposed in one or more additional cross-sectional regions of the fiber.

61. The method of claim 60, wherein the second conductor is disposed in the first and second sets of cross-sectional regions.

62. The method of claim 61, wherein the second conductor electrically contacts the first conductor in the first and second sets of cross-sectional regions.

63. The method of claim 60, wherein the second conductor comprises one or more metals.

64. The method of claim 63, wherein the one or more metals comprise at least one of bismuth, lead, tin, indium, cadmium, gallium, copper, aluminum, silver, gold, and zinc.

65. The method of claim 60, wherein the first conductor has a viscosity that is greater than about $10^2$ Poise at the fiber draw temperature, and the second conductor has a conductivity greater than that of the first conductor.

66. The method of claim 60, wherein the first conductor in each of the first and second sets of cross-sectional regions contacts the material that is in a non-centrosymmetric crystalline phase in the active region, and has a viscosity greater than that of the second conductor.

67. The method of claim 60, further comprising applying an oxidation inhibitor to the second conductor prior to drawing the preform into a fiber.

68. The method of claim 60, further comprising applying a wetting promoter to the second conductor prior to drawing the preform into a fiber.

69. The method of claim 60, further comprising applying a flux to the second conductor prior to drawing the preform into a fiber.

70. The method of claim 52, wherein the relative positions and cross-sectional dimensions of each of the at least three different materials are substantially the same in the preform and the fiber.

71. The method of claim 52, wherein the fiber has a length that is at least about 100 times greater than a length of the preform.

72. The method of claim 52, wherein the fiber has a maximum cross-sectional dimension that is at least about 10 times smaller than a maximum cross-sectional dimension of the preform.

73. The method of claim 52, further comprising consolidating the preform prior to drawing the preform into a fiber.

74. The method of claim 73, wherein consolidating the preform comprises heating the preform under vacuum.

75. The method of claim 52, wherein the fiber draw temperature is greater than a melting temperature or a glass transition temperature of the conductor.

76. The method of claim 52, wherein the fiber draw temperature is between about 120° C. and about 500° C.

77. The method of claim 52, wherein the preform has a length of less than 50 cm.

78. The method of claim 52, wherein the preform is drawn to form a fiber having a length of 1 meter or more.

79. The method of claim 52, wherein the insulator comprises a polymeric insulating material or a high temperature insulating material comprising at least one of silica and silicate glass.

80. The method of claim 79, wherein the polymeric insulating material comprises at least one of a polyimide material, a polysulfone material, a polycarbonate material, a polymethacrylate material, a polyester material, a polyacrylate material, a polyether sulfone material, a cyclic olefin material, and a fluorinated polymer material.

81. The method of claim 52, wherein:
the conductive material comprises a composite of a host material and conducting particulates;
the host material comprises at least one material selected from the group consisting of a polycarbonate material, a polyethylene material, an acrylonitrile-butadiene-styrene copolymer material, an acetal copolymer material, a polypropylene material, a polyvinylidene fluoride material, and a polyetherimide material; and the conducting particulates comprise at least one material selected from the group consisting of carbon particles, carbon fibers, carbon nanotubes, and stainless steel fibers.

82. The method of claim 52, wherein the material that is in a non-centrosymmetric crystalline phase comprises at least one of a poly(vinylidene fluoride) material, a copolymer material of vinylidene fluoride and trifluoroethylene, a polyvinyl chloride material, a copolymer material of vinyl acetate and vinylidene cyanide, a nylon polymer material, a nylon copolymer material, a polyacrylonitrile material, and a high temperature ceramic material comprising at least one of lead zirconate titanate, quartz, barium titanate, and cadmium sulfide.

83. The method of claim 52, wherein assembling the fiber preform comprises wrapping a layer of one of the materials around another one of the materials.

84. The method of claim 52, wherein assembling the fiber preform comprises evaporating a layer of one of the materials or a semiconducting material onto another one of the materials.

85. The method of claim 52, wherein assembling the fiber preform comprises at least one of:
evaporating one or more layers of the conductor onto the material that is in a non-centrosymmetric crystalline phase; and
wrapping one or more layers of the conductor around the material that is in a non-centrosymmetric crystalline phase.

86. The method of claim 52, wherein assembling the fiber preform comprises at least one of:
evaporating a layer of the insulator onto the conductor; and
wrapping a layer of the insulator around the conductor.

87. The method of claim 52, wherein the conductor is a first conductor and the at least three materials further comprise a second conductor, and wherein assembling the fiber preform comprises applying the second conductor to a portion of a surface of the first conductor.

88. The method of claim 87, wherein applying the second conductor to a portion of the surface of the first conductor comprises applying a liquid polymer solution to the portion of the surface of the first conductor, and positioning the second conductor to contact at least a portion of the liquid polymer solution on the first conductor.

89. The method of claim 87, wherein the first and second conductors extend substantially along the entire length of the drawn fiber.

90. The method of claim 52, wherein assembling the fiber preform comprises positioning a sacrificial preform element within the preform to define a hollow fiber region, and removing the sacrificial preform element prior to drawing the preform.

* * * * *